US011439701B2

(12) United States Patent
Huntimer et al.

(10) Patent No.: US 11,439,701 B2
(45) Date of Patent: Sep. 13, 2022

(54) BOVINE RESPIRATORY DISEASE VACCINE

(71) Applicant: Elanco US Inc, Greenfield, IN (US)

(72) Inventors: Lucas Huntimer, Greenfield, IN (US); Thomas Halbur, Greenfield, IN (US)

(73) Assignee: Elanco US Inc, Greenfield, IN (US)

( * ) Notice: Subject to any disclaimer, the term of this patent is extended or adjusted under 35 U.S.C. 154(b) by 0 days.

(21) Appl. No.: 16/610,660

(22) PCT Filed: Apr. 27, 2018

(86) PCT No.: PCT/US2018/029759

§ 371 (c)(1),
(2) Date: Nov. 4, 2019

(87) PCT Pub. No.: WO2018/204178

PCT Pub. Date: Nov. 8, 2018

(65) Prior Publication Data

US 2021/0338799 A1 Nov. 4, 2021

Related U.S. Application Data

(60) Provisional application No. 62/502,004, filed on May 5, 2017.

(51) Int. Cl.

| | |
|---|---|
| ***A61K 39/145*** | (2006.01) |
| ***A61P 31/16*** | (2006.01) |
| ***A61K 39/102*** | (2006.01) |
| ***A61K 39/295*** | (2006.01) |
| *A61K 39/00* | (2006.01) |

(52) U.S. Cl.

CPC .......... *A61K 39/145* (2013.01); *A61K 39/102* (2013.01); *A61K 39/295* (2013.01); *A61P 31/16* (2018.01); *A61K 2039/552* (2013.01)

(58) Field of Classification Search

None

See application file for complete search history.

(56) References Cited

FOREIGN PATENT DOCUMENTS

WO WO17/087492 A1 5/2017

OTHER PUBLICATIONS

Wildman et al., A comparison of 2 vaccination programs in feedlot calves at ultra-high risk of developing undifferentiated fever/bovine respiratory disease, Can Vet Journal, 2008, vol. 49, pp. 463-472.*

Ayalew S et al: Mannheimia haemoloytica chimeric protein vaccine composed of the major surface-exposed epitope of outer membrane lipoprotein P1pE and the neutralizing epitope of leukotoxin:, Vaccine, Elsevier, Amsterdam, NL, vol. 26, No. 38 Sep. 8, 2008, pp. 4955-4961.

Sahlu Ayalew et al: "Immunogenicity of Mannheimia haemolytica recombinant outer membrane proteins serotype 1-specific antigen, 0mpA, 0mpp2, and 0mpd15", Clinical and Vaccine Immunology, vol. 18, No. 12, Dec. 1, 2011, pp. 2067-2074.

Carolina Guzman-Brambila et al: "LKTA and P1pE small fragments fusion protein protect against Mannheimia haemolytica challenge", Research in Veterinary Science., vol. 93, No. 3, Dec. 1, 2012, pp. 1293-1300.

Lucas Ferguson et al: "Pathogenesis of influenza D virus in cattle", Journal of Virology., vol. 90, No. 12, Jun. 15, 2015, pp. 5636-5642.

Hause Ben M et al: An inactivated influenza D virus vaccine partially protects cattle from respiratory disease caused by homologous challenge:, Veterinary Microbiology, vol. 199, Dec. 1, 2016, pp. 47-53.

Ben M. Hause et al., "An inactivated influenza D virus vaccine partially protects cattle from respiratory disease caused by homologous challenge", Vet Microbiol, 2017, pp. 47-53, vol. 199.

Mai Kishimoto et al., "Development of a one-run real-time PCR detection system for pathogens associated with bovine respiratory disease complex", J Vet Med Sci, 2017, pp. 517-523, vol. 79 No. 3.

Eckard Wimmer et al., "Synthetic viruses: a new opportunity to understand and prevent viral disease", Nat Biotechnol, 2009, p. 1163-1172, vol. 27. No. 12.

Anthony W. Confer et al., "Recombinant Mannheimia haemolytica serotype 1 outer membrane protein PlpE enhances commercial M. haemolytica vaccine-induced resistance against serotype 6 challenge", Vaccine, 2006, pp. 2248-2255, vol. 24.

* cited by examiner

*Primary Examiner* — Benjamin P Blumel

(74) *Attorney, Agent, or Firm* — McBee Moore & Vanik IP, LLC; Susan McBee

(57) ABSTRACT

The present invention relates to vaccines for treating bovine respiratory disease. Such vaccines contain a combination of bovine influenza D virus and *Mannheimia haemolytica* antigens. An upper respiratory infection with an IDV leads to an increased potential for *M. haemolytica* pathology in the lungs. The vaccines may contain further antigens from other bovine respiratory pathogens.

13 Claims, No Drawings

Specification includes a Sequence Listing.

BOVINE RESPIRATORY DISEASE VACCINE

The present invention relates to vaccines to treat bovine respiratory disease. Such vaccines contain a combination of bovine influenza D virus antigens and *Mannheimia haemolytica* antigens.

Bovine respiratory disease (BRD) is the most significant disease affecting the United States cattle industry, causing annual losses estimated to be in excess of one billion dollars. Numerous commercial vaccines variably consisting of combinations of inactivated and modified live bacteria and viruses are widely used; however, the incidence of BRD has been increasing for the past several decades. Animal stress, often due to movement and animal management, is thought to predispose cattle to BRD. A number of viruses have established roles in BRD pathogenesis, including bovine viral diarrhea virus, bovine herpesvirus 1, bovine respiratory syncytial virus, bovine parainfluenza virus 3, bovine rhinitis virus, and possibly influenza D virus (IDV) (Ferguson et al, *J. Virol.* 90:5636-42, 2016).

First isolated from pigs with acute respiratory disease, the proposed influenza D virus has subsequently been identified in bovines in numerous countries. Calves inoculated with IDV displayed only mild respiratory disease compared to controls, and virus replication was detected in the respiratory tract associated with a significant increase in neutrophils in the trachea. The highest viral titers were present in the nasal turbinates, decreasing in tissues lower in the respiratory tract. IDV transmitted to contact animals and all inoculated and exposed animals seroconverted. While serological surveys of swine and human sera found low antibody prevalence (9.5 and 1.3%, respectively), several studies have found that IDV antibodies are nearly ubiquitous in bovines, with up to 94% of neonatal beef cattle being seropositive for IDV, likely due to the presence of maternal antibodies. As maternal antibodies are known to interfere with vaccination and the development of active immunity, the presence of antibodies at the time of vaccination may lessen the immune response to a vaccine.

While not conclusively established, IDV may be part of the bovine respiratory disease complex (BRDC). Commercial vaccines for IDV have been suggested, for example in U.S. Pat. No. 9,278,999 and WO2014/015091, but have not been adopted, likely in part due to IDV's recent discovery and its unknown (and possibly minor) role in BRD pathogenesis. Inclusion of IDV into commercial BRD vaccines may improve their efficacy, if IDV infection exacerbates disease caused by other bovine respiratory pathogens, rather than IDV being an opportunistic infection in BRD caused by other pathogens.

The present invention provides for an immunogenic composition comprising a bovine influenza D virus antigen and a *Mannheimia haemolytica* antigen. The combination vaccine provides increased efficacy against BRD compared to monovalent vaccines alone. The *Mannheimia haemolytica* antigen may be an inactivated bacterium, or extracts from inactivated bacteria, such as an outer membrane protein extract. The *Mannheimia haemolytica* antigen may be a recombinantly-produced antigen, such as a recombinant leukotoxin (rLKT).

The present invention provides for an immunogenic composition comprising a bovine influenza D virus antigen and a *Mannheimia haemolytica* antigen, wherein the bovine influenza D virus antigen is an inactivated virus. The bovine influenza D virus antigen may be a modified, live virus. The modified, live bovine influenza D virus antigen may be a modified, live virus modified by codon deoptimization. A modified, live virus modified by codon deoptimization may have one or more deoptimized genomic segments with a cDNA sequence selected from the group consisting of SEQ ID NO:15, SEQ ID NO:16, SEQ ID NO:17, SEQ ID NO:18, and SEQ ID NO:19.

The present invention provides for an immunogenic composition comprising a bovine influenza D virus antigen and a *Mannheimia haemolytica* antigen, which further comprises at least one antigen from an additional bovine pathogen. The additional bovine pathogen may be a bovine viral diarrhea virus (BVDV), bovine respiratory syncytia virus (BRSV), bovine herpesvirus (BHV), parainfluenza virus 3 (PI3), *Pasteurella multocida, Leptospira* species, and *Histophilus somni*, and any combination thereof.

The present invention provides for a vaccine for bovine respiratory disease comprising a bovine influenza D virus and a *Mannheimia haemolytica* antigen, and a pharmaceutically-acceptable excipient, stabilizer, solubilizer, or diluent, and optionally an adjuvant. The *Mannheimia haemolytica* antigen may be an inactivated bacterium, or extracts from inactivated bacteria, such as an outer membrane protein extract. The *Mannheimia haemolytica* antigen may be a recombinantly-produced antigen, such as a recombinant leukotoxin. The bovine influenza D virus antigen may be an inactivated virus. The bovine influenza D virus antigen may be a modified, live virus. The modified, live bovine influenza D virus antigen may be a modified, live virus modified by codon deoptimization.

The present invention provides for a vaccine for bovine respiratory disease comprising a bovine influenza D virus and a *Mannheimia haemolytica* antigen, and a pharmaceutically-acceptable excipient, stabilizer, solubilizer, or diluent, and optionally an adjuvant, which further comprises at least one antigen from an additional bovine pathogen. The additional bovine pathogen may be a bovine viral diarrhea virus (BVDV), bovine respiratory syncytia virus (BRSV), bovine herpesvirus (BHV), parainfluenza virus 3 (PI3), *Pasteurella multocida, Leptospira* species, and *Histophilus somni*, and any combination thereof.

The present invention provides for a method of treating bovine respiratory disease, comprising administering to a bovine an immunogenic composition comprising a bovine influenza D virus antigen and a *Mannheimia haemolytica* antigen. The *Mannheimia haemolytica* antigen may be an inactivated bacterium, or extracts from inactivated bacteria, such as an outer membrane protein extract. The *Mannheimia haemolytica* antigen may be a recombinantly-produced antigen, such as a recombinant leukotoxin. The administering may be done orally, intranasally, intratracheally, or by injection, such as subcutaneously or intramuscularly.

The present invention provides for a method of treating bovine respiratory disease, comprising administering to a bovine an immunogenic composition comprising a bovine influenza D virus antigen and a *Mannheimia haemolytica* antigen, wherein the bovine influenza D virus antigen is an inactivated virus. The bovine influenza D virus antigen may be a modified, live virus. The modified, live bovine influenza D virus antigen may be a modified, live virus modified by codon deoptimization. The administering may be done orally, intranasally, intratracheally, or by injection, such as subcutaneously or intramuscularly.

The present invention provides for a method of treating bovine respiratory disease, comprising administering to a bovine an immunogenic composition comprising a bovine influenza D virus antigen and a *Mannheimia haemolytica* antigen, which further comprises at least one antigen from an additional bovine pathogen. The additional bovine pathogen may be a bovine viral diarrhea virus (BVDV), bovine respiratory syncytia virus (BRSV), bovine herpesvirus (BHV), parainfluenza virus 3 (PI3), *Pasteurella multocida, Leptospira* species, and *Histophilus somni*, and any combination thereof. The administering may be done orally, intranasally, intratracheally, or by injection, such as subcutaneously or intramuscularly.

The present invention provides for a method of treating bovine respiratory disease, comprising administering to a bovine a vaccine for bovine respiratory disease comprising a bovine influenza D virus and a *Mannheimia haemolytica* antigen, and a pharmaceutically-acceptable excipient, stabilizer, solubilizer, or diluent, and optionally an adjuvant. The *Mannheimia haemolytica* antigen may be an inactivated bacterium, or extracts from inactivated bacteria, such as an outer membrane protein extract. The *Mannheimia haemolytica* antigen may be a recombinantly-produced antigen, such as a recombinant leukotoxin. The bovine influenza D virus antigen may be an inactivated virus. The bovine influenza D virus antigen may be a modified, live virus. The modified, live bovine influenza D virus antigen may be a modified, live virus modified by codon deoptimization. The administering may be done orally, intranasally, intratracheally, or by injection, such as subcutaneously or intramuscularly.

The present invention provides for a method of treating bovine respiratory disease, comprising administering to a bovine a vaccine for bovine respiratory disease comprising a bovine influenza D virus and a *Mannheimia haemolytica* antigen, and a pharmaceutically-acceptable excipient, stabilizer, solubilizer, or diluent, and optionally an adjuvant, which further comprises at least one antigen from an additional bovine pathogen. The additional bovine pathogen may be a bovine viral diarrhea virus (BVDV), bovine respiratory syncytia virus (BRSV), bovine herpesvirus (BHV), parainfluenza virus 3 (PI3), *Pasteurella multocida, Leptospira* species, and *Histophilus somni*, and any combination thereof. The administering may be done orally, intranasally, intratracheally, or by injection, such as subcutaneously or intramuscularly.

The present invention provides for the use of a combination of a bovine influenza D virus antigen and a *Mannheimia haemolytica* antigen in treating bovine respiratory disease. The *Mannheimia haemolytica* antigen may be an inactivated bacterium, or extracts from inactivated bacteria, such as an outer membrane protein extract. The *Mannheimia haemolytica* antigen may be a recombinantly-produced antigen, such as a recombinant leukotoxin. The bovine influenza D virus antigen may be an inactivated virus. The bovine influenza D virus antigen may be a modified, live virus. The modified, live bovine influenza D virus antigen may be a modified, live virus modified by codon deoptimization. The treatment may be done orally, intranasally, intratracheally, or by injection, such as subcutaneously or intramuscularly. The treatment may be done therapeutically or prophylactically. The combination may further comprise a pharmaceutically-acceptable excipient, stabilizer, solubilizer, or diluent, and optionally an adjuvant. The combination may further comprise at least one antigen from an additional bovine pathogen. The additional bovine pathogen may be a bovine viral diarrhea virus (BVDV), bovine respiratory syncytia virus (BRSV), bovine herpesvirus (BHV), parainfluenza virus 3 (PI3), *Pasteurella multocida, Leptospira* species, and *Histophilus somni*, and any combination thereof.

The present invention provides for the use of a bovine influenza D virus antigen and a *Mannheimia haemolytica* antigen in the manufacture of a medicament for bovine respiratory disease. The *Mannheimia haemolytica* antigen may be an inactivated bacterium, or extracts from inactivated bacteria, such as an outer membrane protein extract. The *Mannheimia haemolytica* antigen may be a recombinantly-produced antigen, such as a recombinant leukotoxin. The bovine influenza D virus antigen may be an inactivated virus. The bovine influenza D virus antigen may be a modified, live virus. The modified, live bovine influenza D virus antigen may be a modified, live virus modified by codon deoptimization. The medicament may be administered orally, intranasally, intratracheally, or by injection, such as subcutaneously or intramuscularly. The administration may be done therapeutically or prophylactically. The medicament may further comprise a pharmaceutically-acceptable excipient, stabilizer, solubilizer, or diluent, and optionally an adjuvant. The medicament may further comprise at least one antigen from an additional bovine pathogen. The additional bovine pathogen may be a bovine viral diarrhea virus (BVDV), bovine respiratory syncytia virus (BRSV), bovine herpesvirus (BHV), parainfluenza virus 3 (PI3), *Pasteurella multocida, Leptospira* species, and *Histophilus somni*, and any combination thereof.

The present invention provides for a composition comprising a bovine influenza D virus antigen and a *Mannheimia haemolytica* antigen for use in the treatment, reduction or prevention of bovine respiratory disease in a bovine. The *Mannheimia haemolytica* antigen may be an inactivated bacterium, or extracts from inactivated bacteria, such as an outer membrane protein extract. The *Mannheimia haemolytica* antigen may be a recombinantly-produced antigen, such as a recombinant leukotoxin. The bovine influenza D virus antigen may be an inactivated virus. The bovine influenza D virus antigen may be a modified, live virus. The modified, live bovine influenza D virus antigen may be a modified, live virus modified by codon deoptimization. The composition may be administered orally, intranasally, intratracheally, or by injection, such as subcutaneously or intramuscularly. The composition may further comprise a pharmaceutically-acceptable excipient, stabilizer, solubilizer, or diluent, and optionally an adjuvant. The composition may further comprise at least one antigen from an additional bovine pathogen. The additional bovine pathogen may be a bovine viral diarrhea virus (BVDV), bovine respiratory syncytia virus (BRSV), bovine herpesvirus (BHV), parainfluenza virus 3 (PI3), *Pasteurella multocida, Leptospira* species, and *Histophilus somni*, and any combination thereof.

The term “bovine” when used to refer to an animal to which the invention is administered means any member of the genus *Bos*, including domestic cattle (*Bos taurus*).

As used herein “bovine influenza D virus” (IDV) means an RNA virus of the family orthomyxoviridae. IDV is considered to be a separate genus from influenzavirus A, B and C, although IDV appears to be closest related to influenzavirus C. The genome of an IDV contains seven linear negative-sense single-stranded RNA molecules. Two representative isolates of IDV are described in Table 1, without limitation of the invention claimed. As an RNA virus, IDV would be expected to have a high mutation rate leading to a process called “antigenic drift,” small changes in the genome that produce viruses with differing antigenic properties.

As used herein, the term “virus” could mean either the species of virus, or, interchangeably, an individual infectious unit, which may contain nucleic acids, proteins, and a lipid membrane. An individual infectious unit is also called a "viral particle" or a "virion", the latter terms being synonymous.

As used herein, a "strain" or "isolate" a virus means a collection of genetically homologous virions. Two viruses would be considered "homologous" if those viruses map to the same phylogenetic clade. Two viruses would be considered "heterologous" if those viruses map to different phylogenetic clades. The degree of polymorphism among IDV isolates has not yet been evaluated.

TABLE 1

Representative isolates of IDV.

| Segment: | NEB isolate | KS isolate | % identity between isolates |
|---|---|---|---|
| PB2 | 2356 nt[1] SEQ ID NO: 1 | 2337 nt SEQ ID NO: 8 | 99% |
| PB1 | 2261 nt SEQ ID NO: 2 | 2307 nt SEQ ID NO: 9 | 97% |
| P3 | 2194 nt SEQ ID NO: 3 | 2196 nt SEQ ID NO: 10 | 99% |
| HE | 2049 nt SEQ ID NO: 4 | 2045 nt SEQ ID NO: 11 | 96% |
| NP | 1776 nt SEQ ID NO: 5 | 1774 nt SEQ ID NO: 12 | 99% |
| P42 (matrix) | 1219 nt SEQ ID NO: 6 | 1218 nt SEQ ID NO: 13 | 97% |
| NS1 & NS2 | 869 nt SEQ ID NO: 7 | 869 nt SEQ ID NO: 14 | 99% |

[1]nt = nucleotides.

"Percent identity" can be determined by calculating the number of identical nucleotides at the same positions in a nucleic acid. Calculation of percent identity includes determination of the optimal alignment between two or more sequences. Computer programs and algorithms such as the Basic Local Alignment Search Tool (BLAST) may be used to determine the percent identity. BLAST one of the many resources provided by the U.S. National Center for Biotechnology Information. Because the genetic code is degenerate, and more than one codon can encode a given amino acid, coding regions of nucleic acids are considered identical if the nucleic acids encode identical polypeptides.

As used herein, the term "modified, live virus" applies to any individual viral particle (i.e. a "virion") or to a multiplicity of viral particles whose genetic sequence has been altered from the genetic sequence of a naturally-occurring wild type virus. Alterations include, without limitation, genetic mutations such as insertions and deletions of nucleotides and transitions and transversions which change one nucleotide for another nucleotide. Alterations can be accomplished by adapting a wild-type virus to replication in a tissue culture system, and continuing to passage a virus in a tissue culture system, whereby the virus accumulates genetic mutations. Alterations can also be accomplished using molecular techniques. One such molecular technique involves artificially altering the codon usage of a virus, or "codon deoptimization." Such techniques have been described, for example, in U.S. Pat. Nos. 8,846,051; 9,476,032; and US2016/024477 (U.S. Ser. No. 14/777,204), all of which are hereby incorporated by reference in their entirety.

Attenuated viruses form a subset of modified, live viruses. As used herein, the term "attenuated" or "attenuation" means the ability of virus to cause or exacerbate clinical disease has been reduced or eliminated. An attenuated virus can still infect a host cell, either in vitro or in vivo, and that infection may result in subclinical effects in the host organism, but that infection does not result in one or more clinical disease symptoms.

In contrast, as used herein, "inactivated" viruses or bacteria mean pathogens which can no longer replicate in a host. Inactivated pathogens are considered to be killed or dead. Inactivation can be accomplished by a variety of methods, including but not limited to chemical alteration, to chemical or physical alterations in the structure of a pathogen, or to chemical or physical alterations in the pathogen's genomic nucleic acids.

An "antigen" is any molecule capable of being specifically detected by the immune system of an organism. Typically, an antigen is a protein encoded by a pathogen's genome or derived from products of the pathogen's genome. An antigen may be an entire virion or bacterium, or a fraction thereof, or an isolated polypeptide. Antigens may be produced naturally or recombinantly. The presence of antigens can be specifically detected by the surface antigen receptors of both host T lymphocytes and host B lymphocytes and by antibody molecules synthesized by host cells. A non-limiting example of an IDV antigen would be the hemagglutinin-esterase glycoprotein. Non-limiting examples of *Mannheimia* antigens would be an extract of outer membrane proteins (i.e. a mixture of partially purified antigens) and a recombinantly expression leukotoxin polypeptide.

"Immunogenicity" refers to the ability of an antigen to elicit an immune response, said immune response comprising both antigen-specific responses and non-antigen-specific responses or innate immune responses. "Protective immunity" is an immune response which can reduce or prevent clinical symptoms when an immunized animal is challenged or exposed to a pathogenic strain. As one skilled in the art would appreciate, protective immunity may decline with time or increased age of the immunized animal. Protective immunity as used herein should be effective for at least four months, but preferably at least six months, from the latest date of immunization. Protective immunity may be elicited with a single dose of a vaccine. A second or further dose may be used to increase or prolong the protective immune response. For example, increasing the protective immune response in a breeding cow may result in an increased level of maternally derived antibody in calves.

In contrast to an antigen, an "adjuvant" is a non-specific stimulator of an immune response. An adjuvant could stimulate the innate immune response by binding and activating a pattern recognition receptor (PRR). Such stimulators of PRRs could be, for example, viral or bacterial nucleic acids, lipids from bacteria or parasites, or bacterial proteins or toxins, or any artificially-constructed mimic of such molecules. Adjuvants also include, without limitation: inorganic compounds that aggregate antigens to facilitate recognition by B lymphocytes or uptake by phagocytes, such as alum, aluminum hydroxide, aluminum phosphate, calcium phosphate hydroxide or ammonium sulfate; oils; and detergents. Adjuvants could also be host mediators of immune signaling, such as, without limitation, cytokines, lymphokines, chemokines, interferons, anaphylatoxins, growth factors, differentiation factors, and adhesion molecules.

As used herein, an "immunogenic composition" is a composition that elicits an immune response when administered to an animal. An immunogenic composition comprises at least one antigen and at least one pharmaceutically-acceptable excipient, stabilizer, solubilizer, or diluent. A description of pharmaceutically-acceptable excipients, stabilizers, solubilizers, or diluents can be found, for example, in "Remington: The Science and Practice of Pharmacy," Lloyd V. Allen, ed., Pharmaceutical Press, London, UK, 22nd edition, 2012. The antigen can be a whole virus, bacterium, or other pathogen, either live or inactivated. The antigen can also be isolated, purified, or a partially purified antigenic molecule from a virus, bacterium, or other pathogen. The antigen can be a polypeptide, a polysaccharide, a nucleic acid, or a lipid. The antigen is at least partially isolated from its natural environment, which could include factors capable of diluting, misdirecting or interfering with an effective immune response to the antigen.

As used herein, a "vaccine" is an immunogenic composition which stimulates an animal's immune system to develop protection from, resistance to, prevention of, or treatment for a disease symptom when administered to an animal in need thereof, wherein said symptom is caused by a pathogenic organism, for example a virus or a bacterium. A vaccine may include, without limitation, viral antigens or intact virions, either live or inactivated, in composition with pharmaceutically-acceptable adjuvants, excipients, stabilizers, solubilizers, or diluents, and optionally an adjuvant. A vaccine may include, without limitation, bacterial antigens or intact bacteria, either live or inactivated, in composition with pharmaceutically-acceptable adjuvants, excipients, stabilizers, solubilizers, or diluents, and optionally an adjuvant. A vaccine may include multiple antigens from multiple pathogens.

As used herein, the terms "treating", "to treat", or "treatment", include restraining, slowing, stopping, reducing, ameliorating, or reversing the progression or severity of an existing symptom, disorder, condition, or disease. A treatment may be applied prophylactically or therapeutically.

As used herein, "administering" includes but is not limited to cutaneous, subcutaneous, intramuscular, mucosal, submucosal, transdermal, intratracheal, oral or intranasal administration. Administration could occur by injection or by topical administration.

The following experimental examples are illustrative of bovine respiratory disease vaccines. It will be appreciated that other embodiments and uses will be apparent to those skilled in the art and that the invention is not limited to these specific illustrative examples or preferred embodiments.

EXAMPLE 1

This study evaluated if respiratory pathogenesis develops in 6-9 month old cattle when administered a high titer influenza D virus (IDV) and if that pathogenesis can be mitigated by a homologous inactivated vaccine.

A total of 83 Holstein or Holstein cross cattle approximately 6 months old were used for this study. The animals were allowed to acclimate for a minimum of 5 days to their new environment at the testing facility. Housing consisted of an ABSL-2 containment room, with common feed line bunk and open water tank system in each room. The animals met the following inclusion criteria: BVDV-PI negative via ear notch and antigen capture ELISA (ACE); in good health based on physical examination conducted on Day 0; and seronegative to IDV. Animals were randomly allocated to treatment groups (Table 2) using a random allocation plan. Study personnel conducting clinical observations, collecting samples and analyzing samples were masked to treatment identity. Following administration of each treatment (e.g. vaccination), animals were housed by treatment group such that each group was in an isolated pen with no physical contact between each treatment group, with the exception of calves from treatment group four (T04), which were co-housed with challenged cattle (groups T02 and T03).

TABLE 2

Experimental design.

| Treatment groups | Vaccination day | Challenge 35 d | Serology 14-96 d | Serial slaughter Groups (post-challenge days) 37 d (2) | 39 d (4) | 41 d (6) | 43 d (8) | 45 d (10) |
|---|---|---|---|---|---|---|---|---|
| T01 | 0, 14 | No | 10 head (hd) | 3 hd | 3 hd | 3 hd | 3 hd | 3 hd |
| T02 | No | IDV | — | 5 hd | 5 hd | 5 hd | 5 hd | 5 hd |
| T03 | 0, 14 | IDV | — | 5 hd | 5 hd | 5 hd | 5 hd | 5 hd |
| T04 | No | No | — | — | — | — | 3 hd | 4 hd |

The experimental vaccine comprised beta-propriolactone (BPL) inactivated IDV strain D/Bovine/KS/14-22/2012. Vaccine was standardized to 640 hemagglutinatin units (HAU) per dose. Antigen was batched and formulated/adjuvanted with 30% EMULSIGEN® D. The vaccine underwent a modified sterility test consisting of final product being plated on blood agar, incubated at 37° C. and examination of colonies formed approximately 48 hours later. No colonies were identified and product considered sterile. Calves were vaccinated (2.0 mL) by subcutaneous (SQ) injection on the right side of the neck (20-gauge 1-inch needle) on Day 0 and Day 14. Animals were observed at approximately one (1) hour post-vaccination to assess response to vaccination. No abnormal events were noted.

Challenge occurred on Day 35 (~7 months of age). On Day 35 (35 d) each calf was challenged intranasally (5.0 ml; 2.5 mL/nostril) with IDV strain D/Bovine/KS/14-22/2012 at $10^6$ $TCID_{50}$.

All animals were evaluated for depression, body condition and respiratory distress on Days 35 through necropsy and scored. Animals were evaluated and scores recorded prior to movement or feeding. Rectal body temperatures were recorded daily during the challenge period (Day 35-45). Temperatures were recorded at approximately the same time each day. One blood sample was collected at least 7 days prior to arrival at the facility and the rest of the blood samples for the determination of IDV hemagglutination inhibition were collected on Days 0, 14, 21, 28, 35, 42, 49, 56, 63, 70, 84, 98, 112. One nasal swab sample was collected at least 7 days prior to arrival at the facility and the rest of the nasal swabs were collected from all animals on Days 35 (pre-challenge), 37, 39, 41, 43, and 45. Swabs were placed into a tube containing transport medium. Tubes were labeled with date of collection, animal identification (ear tag number), sample type (nasal), and study number. Tubes were cooled immediately by placing them into a cooler containing ice packs. The tubes were stored at −70° C.

On Days 35, 37, 39, 41, 43, and 45, the respective animals were humanely euthanized for lung lesion scoring, collection of bronchoalveolar lavage (BAL) fluid, and the respective tissue. Lungs were removed from each animal. BAL fluid was collected aseptically from the excised lungs. Sterile phosphate buffered saline (PBS) was pipetted into the lungs and pipetted back as the lungs are gently massaged. The BAL fluid extracted was placed into a tube kept on ice. Each sample of BAL fluid was divided into two aliquots and labeled with animal ID and date of sample collection. Both set of aliquots were stored frozen (≤−20° C.).

Each of the seven pulmonary lobes was examined both visually and by palpation for gross characteristic lesions attributable to IDV. The amount of lesion/consolidation in each pulmonary lobe was scored and recorded as an actual value between 0 and 100% of the lobe. The amount of lesion (score) in each lobe was inserted in a weighted formula in order to calculate the percentage of lung with lesions. The weight assigned to each of the seven lobes (according to the relative weight of the lung lobes) is as follows: left apical lobe=10%; left cardiac lobe=10%; left diaphragmatic lobe=25%; right apical lobe=10%; right cardiac lobe=10%; right diaphragmatic lobe=25%; and accessory lobe=10%. The addition of the weighted percentages resulted in a composite lung lesions score.

Lung, turbinate, and tracheal tissues were examined at necropsy for lesions and a section was excised for immunohistochemistry. The tracheobronchial lymph node was excised for immunohistochemistry evaluation as well. All samples were stained with hematoxylin and eosin for structural evaluation as well as stained for IDV virus using standard immunohistochemistry techniques.

Nasal swabs were evaluated for IDV virus via RT-PCR using a specific primer set developed by the Kansas State University (KSU) veterinary diagnostic laboratory. The mean with standard deviation of the threshold cycle (CT) value of the tested nasal swabs were extrapolated using a standard curve of known tissue culture infectious dose ($TCID_{50}$) IDV virus to produce a viral titer value of the nasal swabs. The CT value was extrapolated using a standard curve of known tissue culture infectious dose ($TCID_{50}$) IDV virus to produce a viral titer value (Table 3).

Bronchioalveolar lavage fluid (Table 4) and tracheal swabs (from days 41, 43, and 45) (Table 5) were also evaluated for IDV virus via RT-PCR, and the CT value was extrapolated using a standard curve of known tissue culture infectious dose ($TCID_{50}$) IDV virus to produce a viral titer value for each sample group.

TABLE 3

Nasal Swab Viral Titer ($TCID_{50}$).

| Treatment Group | At challenge | 2 DPC[1] | 4 DPC | 6 DPC | 8 DPC | 10 DPC |
|---|---|---|---|---|---|---|
| T01- Vaccination+ Challenge− | 0 | 0 | 0 | 0 | 0 | 0 |
| T02- Vaccination− Challenge+ | 0 | 2.64 | 5.68 | 3.765 | 0.24 | 0.275 |
| T03- Vaccination+ Challenge+ | 0 | 1.52 | 3.98 | 2.01 | 1.23 | 0 |
| T04- Contact Controls | 0 | 0 | 0.65 | 0.78 | 3.34 | 4.95 |

[1]Days post challenge (DPC).

TABLE 4

Tracheal Swab Viral Titer ($TCID_{50}$).

| Treatment Group | 6 DPC | 8 DPC | 10 DPC |
|---|---|---|---|
| T01- Vaccination+ Challenge− | 0 | 0 | 0 |
| T02- Vaccination− Challenge+ | 5.34 | 0.64 | 0.18 |
| T03- Vaccination+ Challenge+ | 1.72 | 0.64 | 0 |
| T04- Contact Controls | NA | 4.63 | 3.3 |

Assessments of the upper respiratory tract and lung lesion scoring as outlined above were taken by the blinded study investigator. Composite lung lesions scores are outlined in Table 6 as mean composite scores/number of animals per group at each time point.

TABLE 5

BALF Viral Titer ($TCID_{50}$).

| Treatment Group | 2 DPC | 4 DPC | 6 DPC | 8 DPC | 10 DPC |
|---|---|---|---|---|---|
| T01- Vaccination+ Challenge− | 0 | 0 | 0 | 0 | 0 |
| T02- Vaccination− Challenge+ | 0.54 | 2.68 | 4.98 | 1.52 | 1.26 |
| T03- Vaccination+ Challenge+ | 0 | 1.22 | 0 | 0 | 0 |
| T04- Contact Controls | NA | NA | NA | 1.73 | 3.15 |

TABLE 6

Mean Composite Lung Lesion Scores

| Treatment Group | 2 DPC | 4 DPC | 6 DPC | 8 DPC | 10 DPC |
|---|---|---|---|---|---|
| T01- Vaccination+ Challenge− | 0.59/3 | 0.00/3 | 0.24/3 | 0.06/3 | 0.04/3 |
| T02- Vaccination− Challenge+ | 0.29/5 | 1.01/5 | 2.46/5 | 0.64/5 | 1.70/5 |
| T03- Vaccination+ Challenge+ | 0.18/5 | 0.72/5 | 1.34/5 | 0.58/5 | 1.04/5 |
| T04- Contact Controls | NA | NA | NA | 0.59/3 | 0.15/2 |

Mild lung lesion scores were observed with slight trending differences between the vaccinates versus challenged animals. Stronger statistical power could be added as well as refinement of the challenge model to further explore the gross lung pathology caused by IDV. Gross pathological examinations of the upper respiratory tract, exclusively the trachea demonstrated a mucoid exudate with peak observations at 4 and 6 days post challenge.

Fixed tissue samples from the nasal turbinate and the trachea were processed, hematoxylin and eosin stained, and then stained with antibody specific for IDV virus. The number of positive samples out of total number of animals per group for nasal turbinate samples and for trachea samples are represented in Tables 7 and 8, respectively.

TABLE 7

Immunohistochemistry Results (number positive) of Nasal Turbinate Samples

| Treatment Group | 2 Days Post Challenge (DPC) | 4 DPC | 6 DPC | 8 DPC | 10 DPC |
|---|---|---|---|---|---|
| T01- Vaccination+ Challenge− | 0/3 | 0/3 | 0/3 | 0/3 | 0/3 |
| T02- Vaccination− Challenge+ | 1/5 | 1/5 | 5/5 | 1/5 | 0/5 |
| T03- Vaccination+ Challenge+ | 0/5 | 0/5 | 0/5 | 0/5 | 0/5 |
| T04- Contact Controls | NA | NA | NA | 1/3 | 2/2 |

TABLE 8

| Immunohistochemistry Results (number positive) of Trachea Samples | | | | | |
|---|---|---|---|---|---|
| Treatment Group | 2 Days Post Challenge (DPC) | 4 DPC | 6 DPC | 8 DPC | 10 DPC |
| T01- Vaccination+ Challenge− | 0/3 | 0/3 | 0/3 | 0/3 | 0/3 |
| T02- Vaccination− Challenge+ | 0/5 | 4/5 | 5/5 | 0/5 | 0/5 |
| T03- Vaccination+ Challenge+ | 0/5 | 2/5 | 0/5 | 0/5 | 0/5 |
| T04- Contact Controls | NA | NA | NA | 1/3 | 0/2 |

Serological antibody titers were assessed at study day (SD) 0, 14, 21, 28, 35, and 42 for serological conversion to the vaccine. Geometric mean titer (GMT) of hemagglutination inhibition (HI) titer of the serum from each group is depicted in Table 9. Serological evaluation shows there was an increase in HI titer against IDV in the vaccinated groups compared to the non-vaccinates. Routine dose and vaccine optimization could be evaluated further to possibly increase the antibody titer. For comparison, in humans a HI titer of 40 (5.3 $\log_2$) is generally considered protective against influenzavirus A infection but does not fully alleviate disease symptoms.

TABLE 9

| Hemagglutination Inhibition (HI) Serum Titer ($\log_2$). | | | | | | |
|---|---|---|---|---|---|---|
| Treatment Group | At challenge | 14 DPC | 21 DPC | 28 DPC | 35 DPC | 42 DPC |
| T01- Vaccination+ Challenge− | 28 | 58.7 | 154.7 | 210.7 | 160 | 160 |
| T02- Vaccination− Challenge+ | 28.8 | 37.6 | 24 | 32 | 34.4 | 40 |
| T03- Vaccination+ Challenge+ | 28.8 | 49.6 | 132.8 | 201.6 | 208 | 328 |
| T04- Contact Controls | 32 | 48 | 32 | 36 | 40 | 36 |

Clinical observations of depression and body condition scoring were mostly unremarkable. Respiratory distress was demonstrated in the challenged animals with peak clinical signs at 6 days post challenge. No differences in respiratory distress between vaccinated and unvaccinated animals were observed.

The primary objective of this study was to assess if bovine influenza D virus (IDV) was capable of eliciting clinical pathogenesis and discover if a homologous inactivated vaccine preparation was able to prevent the clinical pathogenesis. In animals challenged with IDV, replication of the virus took place in the upper respiratory tract based on RT-PCR. The kinetics of viral replication indicate that the highest viral titers were shown at 6 days post challenge. The amount of virus was trending towards being higher in the nasal swabs, tracheal swabs, and the BALF of treatment group 2 (T02) as compared to the vaccinated groups with the greatest differences in the tracheal swabs and BALF samples. Additionally, immunohistochemistry staining of IDV was performed on the fixed excised tissues of the upper respiratory tract (turbinate and trachea). Challenged animals were positive for IDV virus via staining with five of five cattle being positive at 6 days post challenge. No animals receiving vaccine were positive for IDV via IHC staining. It can be hypothesized that immunization may limit the amount of viral spread by reducing the viral load in the upper respiratory tract. Further, the contact control group (T04) showed that the virus was passed from the challenged animals (T02) to co-housed naïve animals.

Based on the results of this study IDV appears to replicate in the upper respiratory tract and elicit a mild inflammation based on immunohistochemical observations. This viral infection may be an important contributor to the bovine respiratory disease complex in which preventive intervention like vaccines could increase overall cattle health.

EXAMPLE 2

This study evaluated the hypothesis that the upper respiratory infection caused by Influenza D virus is a precursor to, or exacerbator of, a more severe secondary *Mannheimia haemolytica* infection.

A total of 70 Holstein or Holstein cross cattle 5-9 months old were used for this study. The animals were allowed to acclimate for a minimum of 5 days to their new environment at the testing facility. Housing consisted of an ABSL-2 containment room, with common feed line bunk and open water tank system in each room. The animals met the following inclusion criteria: BVDV-PI negative via ear notch and antigen capture ELISA (ACE); in good health based on physical examination conducted on Day 0; seronegative to IDV; and seronegative to leukotoxin (LKT) of *M. haemolytica.*

The IDV experimental vaccine comprised BPL inactivated IDV strain D/Bovine/NE/103795/2012. The strain of influenza virus used for immunizations and challenge was changed from D/Bovine/KS/14-22/2012 to D/Bovine/NE/103795/2012 due to the latter virus growing better for scale up. Vaccines were standardized to 1280 HAU per dose. Antigen was batched and formulated/adjuvanted 1:1 weight by weight with SEPPIC MONTANIDE ISA 201 VG. The vaccine underwent a 7-day media bottle sterility test in Fluid Thioglycollate Media (FTM) and Tryptic Soy Broth (TSB) broth prior to use.

The *M. haemolytica* vaccine comprised an inactivated outer membrane proteins (OMP) extract and recombinant LKT (rLKT). Vaccines were standardized to 250 μg of OMP and 125 μg of LKT per dose. Antigen was batched and formulated/adjuvanted 1:1 weight by weight with SEPPIC MONTANIDE ISA 201 VG. The vaccine underwent a 7-day media bottle sterility test in FTM and TSB broths prior to use.

TABLE 10

| Treatment groups. | | | | | | |
|---|---|---|---|---|---|---|
| Treatment Group | Vaccine (SD 0 & 14) | Animals/ Treatment | Dose/ Route | IDV Challenge (SD 35) | *M. haemolytica* Challenge (SD 41) | Necropsy and Lung Scores (SD 48) |
| T01 | Adjuvanted Saline | 10 | 2 mL/SC | + | +* | + |
| T02 | Saline | 10 | 2 mL/SC | + | − | + |
| T03 | Saline | 9 | 2 mL/SC | − | +* | + |

TABLE 10-continued

| Treatment groups. | | | | | | |
|---|---|---|---|---|---|---|
| Treatment Group | Vaccine (SD 0 & 14) | Animals/ Treatment | Dose/ Route | IDV Challenge (SD 35) | *M. haemolytica* Challenge (SD 41) | Necropsy and Lung Scores (SD 48) |
| T04 | Adjuvanted Saline | 10 | 2 mL/SC | − | +** | + |
| T05 | IDV vaccine | 10 | 2 mL/SC | + | +* | + |
| T06 | *M. haemolytica* vaccine | 10 | 2 mL/SC | + | +* | + |
| T07 | *M. haemolytica* + IDV vaccine | 10 | 2 mL/SC | + | +* | + |

**Mannheimia haemolytica* challenge administered intranasally with disposable atomizer (5.0 mL; 2.5 mL/nostril) and 5.0 mL intratracheally with endoscope to be delivered at the larynx/trachea
***Mannheimia haemolytica* challenge administered intratracheally by locating the bifurcation of the trachea and pulling back approximately 10 cm and delivering 60 mL with *M. haemolytica* strain The combination vaccine comprised BPL inactivated IDV strain D/Bovine/NE/103795/2012 plus inactivated outer membrane proteins (OMP) extract and rLKT. Vaccines were standardized to 1280 HAU per dose of IDV, 250 µs of OMP, and 125 of LKT per dose. Antigens were batched and formulated/adjuvanted 1:1 weight by weight with SEPPIC MONTANIDE ISA 201 VG. The vaccine underwent a 7-day media bottle sterility test in FTM and TSB broth prior to use.

All candidate animals that met selection criteria and inclusion/exclusion criteria were eligible for enrollment. Animals were randomly allocated to treatment groups using a random allocation plan. Study personnel conducting clinical observations, collecting samples and analyzing samples were masked to treatment identity. The study investigator who performed the lung lesion scoring was blinded to the specific calf ID during scoring.

Following arrival at the study site, animals were housed within three ABSL-2 containment rooms. Groups T01, T02, T05, T06 and T07 were housed in two rooms (25 animals per room) with equal representation of treatment groups between rooms. Groups T03 and T04 were housed in a separate third room to prevent shedding of IDV from challenged animals to cross contaminate IDV naïve animals. Animals were comingled within the three rooms. Following *M. haemolytica* challenge on study day 41 (SD41) the entire herd was resorted to equally distribute treatment groups (T01-T07) between the three ABSL-2 containment rooms with 23-24 animals per room. Equal representation of each treatment group (3-4 animals per group per room) was obtained following the resort. Calves were vaccinated (2.0 mL) by subcutaneous (SQ) injection on the right side of the neck (18-gauge 1-inch needle) on Day 0 and left side of the neck on Day 14. Animals were observed at approximately one (1) hour post-vaccination to assess response to vaccination. Study animals were observed daily to determine general health status beginning on Day −5 and continuing through Day 48. Observations were made at approximately the same time each day. Animal health observations consisted of pen-side visual assessments of animals for indicators of animal health.

Influenza D Virus challenge occurred on Day 35 (~6-10 months of age) for Groups T01, T02, T05, T06, and T07. On Day 35, each calf was challenged intranasally with disposable PREVAL® can atomizer (10.0 mL; 5 mL/nostril) with IDV strain D/Bovine/NE/103795/2012 at $10^{5.7}$ $TCID_{50}$.

IDV was produced as follows. Three 850 $cm^2$ tissue culture polystyrene roller bottles were planted with ST-C cells at a target density of $2\times10^7$ cells/bottle (i.e. 23529 cells/$cm^2$) in EMEM media with 7.5% FBS and 4 mM L-glutamine. The roller bottles rotated at 0.25 rpm at 37° C. After 7 days, the cells were infected. To infect, the used media was first replaced with pre-warmed EMEM media only, and IDV (D/Bovine/NE/103795/2012) was added at a multiplicity of infection (MOI) of 0.05. After an additional 3 days of incubation at 0.25 rpm and 37° C., the entire roller bottle and contents were harvested by freezing at −80° C., thawing and dispensed aseptically.

At time of harvest, samples were taken for virus titer assay. To assay, ST-C cells were planted at 15,000 cells/well in 96-well plates. 3 days post-planting, when the cells were ~95% confluent, the wells were washed with PBS two times before 100 µL EMEM with 0.2 mL/L gentamicin was added to each well. Next, the harvested IDV samples were serially diluted 1:10 before 100 µL of each dilution was added to each well. After an additional 3 days of incubation at 37° C. and 5% $CO_2$, the plates were fixed with 80% acetone at −20° C. for at least 20 minutes, before being dried at 37° C. For staining, the primary antibody was diluted in D-PBS, added to each well, and incubated at 37° C. for 1 hour. Following three washes in PBS, the secondary antibody was diluted in D-PBS, added to each well, and incubated at 37° C. for 75 minutes. After two washes in PBS, the results were obtained visually under a fluorescent microscope and calculated via the Spearman-Karber equation.

*Mannheimia haemolytica* Challenge occurred on Day 41 (~6-10 months of age) for Groups T01, T03, T04, T05, T06, and T07. On Day 41, each calf from Groups T01, T03, T05, T06, and T07 was challenged intranasally with a disposable atomizer (5.0 mL; 2.5 mL/nostril) and 5.0 mL intratracheally with an endoscope at the larynx/trachea bifurcation with *M. haemolytica* strain at $10^9$ CFU/mL. On Day 41, each calf from Group T04 was challenged intratracheally by locating the bifurcation of the trachea and pulling back approximately 10 cm and delivering 60 mL of *M. haemolytica* strain at $10^9$ CFU/mL with endoscope.

Rectal body temperatures were recorded daily during the challenge period (Day 35-48). Temperatures were recorded at approximately the same time each day.

One blood sample was collected at a minimum of 7 days prior to arrival at the facility and the rest of the blood samples for the determination of IDV hemagglutination inhibition and anti-*M. haemolytica* LKT antibody were collected on Days −2, 14, 21, 28, 35, 41, and 48.

One nasal swab sample was collected at a minimum of 7 days prior to arrival at the facility and the rest of the nasal swabs were collected from all animals on Days 35 (pre-challenge), 37, 39, 41, 43, 45 and 47. In addition, swabs of the trachea were obtained at necropsy on Day 48.

On Day 48, the indicated animals were humanely euthanized for lung lesion scoring, collection of bronchoalveolar lavage (BAL) fluid, and tissue collection. Lungs were removed from each animal, and BAL fluid was collected aseptically from the excised lungs. Sterile phosphate buffered saline (PBS) was pipetted into the lungs and collected by pipette as the lungs were gently massaged. The BAL fluid extract was placed into a tube kept on ice. Each sample of BAL fluid was divided into two aliquots and labeled with animal ID and date of sample collection. Both set of aliquots were stored frozen (≤−20° C.).

Each of the seven pulmonary lobes was examined both visually and by palpation for gross characteristic lesions attributable to *M. haemolytica* and/or IDV. The amount of lesion/consolidation in each pulmonary lobe was scored and recorded as an actual value between 0 and 100% of the lobe. The amount of lesion (score) in each lobe was inserted in a weighted formula in order to calculate the percentage of lung with lesions. The weight assigned to each of the seven lobes (according to the relative weight of the lung lobes) is as follows: left apical lobe=10%; left cardiac lobe=10%; left diaphragmatic lobe=25%; right apical lobe=10%; right cardiac lobe=10%; right diaphragmatic lobe=25%; and accessory lobe=10%.

Nasal turbinates, trachea, tracheobronchial lymph node, and lung tissues were examined at necropsy for lesions and a section of each was excised. The section was divided so that one half was placed in fixative (buffered formalin or equivalent) for immunohistochemistry evaluation as well as stained with hematoxylin and eosin for structural evaluation, and the other half will be placed in RNALATER® or frozen at −70° C. for cytokine and inflammatory gene PCR analysis.

The primary variable, total percent lung lesion score on SD48, was calculated and analyzed as in Example 1. Secondary variables were summarized or analyzed including daily depression scores, daily body condition score, daily respiratory score and daily rectal body temperature from SD 35 to SD48 was well as mortality and removals from SD 35 to SD48.

Data from the seven treatments T01, T02, T03, T04, T05, T06 and T07 were pooled and analyzed. For each variable, calculations were done on a per animal basis because the animal was the experimental unit. All testing was conducted at the 5% significance level unless otherwise stated.

Total percent lung lesion scores on Day 48 were transformed using arsin (sqrt(Total Percent Lung Score)) and were analyzed using a linear mixed model analysis (SAS® PROC MIXED v 9.4 or higher), with fixed effect, per treatment. Linear contrasts were conducted using the following pairwise comparisons:

T01 vs. T02, T03, T04;

T02 vs. T03, T04;

T03 vs. T04; and

T04 vs. T05, T06, and T07.

Least squares means (LSMEANs) and standard errors as well as arithmetic means and standard deviations were calculated for each treatment group and back-transformed results are presented.

In addition, summary statistics were presented for the mitigated fractions (MF) (R version 3.0.3 (2014 Mar. 6)). Frequency distributions of daily depression scores, daily body condition score and daily respiratory scores were obtained for each time by treatment.

There were two mortalities due to morbidity, both in Treatment Group 4. No other groups had mortalities.

The primary objective of this study was to evaluate the mortality and lung lesion scores of the different treatment groups and to evaluate the hypothesis that the upper respiratory infection caused by Influenza D virus is a precursor to a more severe secondary *Mannheimia haemolytica* infection. Mean lung lesion scores of animals challenged intranasally with *M. haemolytica* following an Influenza D virus challenge showed a greater than fourfold increase compared to animals intranasally challenged with *M. haemolytica* alone (Group T01=5.6 and Group T03=1.2 respectively). This supports the hypothesis that an upper respiratory infection with an IDV leads to an increased potential for *M. haemolytica* to migrate from the upper respiratory tract where it typically colonizes to the lower respiratory tract and lungs where pathology starts to be exhibited.

The mean lung lesion score in the IDV and *M. haemolytica* challenged cattle was lower than what is observed in the traditional model of *M. haemolytica* infection in which a larger volume of bacteria (60 mL compared to 10 mL intranasal/intratracheal) is delivered directly to the lungs. The differences in the severity can be explained by the decreased dose and the anatomical and mechanical immunological defenses between the upper respiratory tract and the lungs.

TABLE 11

Mean Lung Lesion Scores

| Treatment Group | Vaccine (SD 0 & 14) | IDV Challenge (SD 35) | *M. haemolytica* Challenge (SD 41) | Mean Lung Scores |
|---|---|---|---|---|
| T01 | Adjuvanted Saline | + | +* | 5.6 |
| T02 | Saline | + | − | 0.5 |
| T03 | Saline | − | +* | 1.2 |
| T04 | Adjuvanted Saline | − | +** | 23.9 |
| T05 | IDV vaccine | + | +* | 2.5 |
| T06 | *M. haemolytica* vaccine | + | +* | 0.9 |
| T07 | *M. haemolytica* + IDV vaccine | + | +* | 0.1 |

**Mannheimia haemolytica* challenge administered intranasally with disposable atomizer (5.0 mL; 2.5 mL/nostril) and 5.0 mL intratracheally with endoscope was delivered at the larynx/trachea

***Mannheimia haemolytica* challenge administered intratracheally by locating the bifurcation of the trachea and pulling back approximately 10 cm and delivering 60 mL with *M. haemolytica* strain

TABLE 12

Mitigated Fraction Statistical Analysis of Lung Lesion Scores

| Group | versus Group | MF | Lower Bound | Upper Bound |
|---|---|---|---|---|
| T04 | T05 | 0.90 | 0.66 | 1.00 |
| T04 | T06 | 0.92 | 0.70 | 1.00 |
| T04 | T07 | 1.00 | 1.00 | 1.00 |
| T01 | T05 | 0.42 | −0.06 | 0.83 |
| T01 | T06 | 0.44 | −0.06 | 0.86 |
| T01 | T07 | 0.70 | 0.28 | 1.00 |

Additionally, a combination inactivated vaccine containing both IDV and *M. haemolytica* antigens provided statistically significant protection (as measured by MF) to the dual challenge of lung lesion scoring that would be considered efficacious as the current statistical criteria outlines for *M. haemolytica* models used to license vaccines (>0.4 MF with positive upper and lower bounds). Monovalent vaccines of IDV (mean lung lesion score of 2.5) and *M. haemolytica* (mean lung lesion score of 0.9) provided a MF above the criteria but the upper and lower confidence bounds did not meet the satisfactory criteria. Therefore, a combination vaccine of IDV and *M. haemolytica* is an effective approach to controlling bovine respiratory disease.

What is claimed is:

1. An immunogenic composition comprising a bovine influenza D virus antigen and a *Mannheimia haemolytica* antigen.

2. The immunogenic composition of claim 1, wherein the *Mannheimia haemolytica* antigen is selected from the group of an inactivated bacterium, an extract of outer membrane proteins, and a recombinant leukotoxin, and any combination thereof.

3. The immunogenic composition of claim 1, wherein the bovine influenza D virus antigen is an inactivated virus.

4. The immunogenic composition of claim 1, wherein the bovine influenza D virus antigen is a modified, live virus.

5. The immunogenic composition of claim 4, wherein the modified, live bovine influenza D virus antigen is a modified, live virus modified by codon deoptimization.

6. The immunogenic composition of claim 4, wherein the modified, live bovine influenza D virus antigen comprises at least one codon-deoptimized genomic segment having a cDNA sequence selected from the group consisting of SEQ ID NO: 15, SEQ ID NO:16, SEQ ID NO:17, SEQ ID NO:18, and SEQ ID NO:19.

7. A vaccine for bovine respiratory disease comprising a bovine influenza D virus antigen and a *Mannheimia haemolytica* antigen, and a pharmaceutically acceptable excipient, stabilizer, solubilizer, or diluent, and optionally an adjuvant.

8. The vaccine of claim 7, further comprising at least one antigen from an additional bovine pathogen.

9. The vaccine of claim 8, wherein the additional bovine pathogen is selected from the group of bovine viral diarrhea virus (BVDV), bovine respiratory syncytia virus (BRSV), bovine herpesvirus (BHV), parainfluenza virus 3 (PB), *Pasteurella multocida, Leptospira* species, and *Histophilus somni*, and any combination thereof.

10. A method of treating or preventing bovine respiratory disease, comprising administering to a bovine the immunogenic composition of claim 1.

11. The method of claim 10, wherein the administering is done orally, intranasally, intratracheally, or by injection.

12. A method of treating or preventing bovine respiratory disease, comprising administering to a bovine the vaccine of claim 7.

13. The method of claim 12, wherein the administering is done orally, intranasally, intratracheally, or by injection.

* * * * *

SEQUENCE LISTING

<160> NUMBER OF SEQ ID NOS: 19

<210> SEQ ID NO 1
<211> LENGTH: 2356
<212> TYPE: DNA
<213> ORGANISM: Artificial Sequence
<220> FEATURE:
<223> OTHER INFORMATION: cDNA from influenza D virus

<400> SEQUENCE: 1
cagaggatgt caccactatt aacgctcgca aaagagtatg caaatctcac aaaggataag 60
aaatcatgca aattgctgtc gcaagggacc gtgtcaagct acaccacttt taagaaatgg 120
acaacatcga gaaaagagaa aaacccatcc cttcgaatga gatgggcaat gggaagcaag 180
ttcccaatca tggcaaacag agaaattttg gaagaagctg ggataccaga acaatgggaa 240
gggatagacc tttggtcaaa aaggatgat gtttcaaagt tggggatggt gttagcgtct 300
cccgcagcca taacttactg gaatttttgt ggacctggag tggacaattc ttctgtaata 360
agggatgttt acaaagcaaa atttatgaaa aaagagagat ggagagagac tctgtgggga 420
ccaatgaact ttgaactggt gggtaaacaa agaagagtgg ttgaaactca accagtggaa 480
ataaaactaa accaaaaaga aataaaagaa ctaacgatgt gggttctttt tgaggatgaa 540
gcaaaccttg caagcaaatt catacaggaa aatttctcac ttgtcctgtc attaagagaa 600
ctttacaagg gaaaggcagt aaataaagat gttgcagctt ttatgattgc acaccaattt 660
tctcccgaga agaggttctt acccactttt ggccccatta gaccagaaag gatggagcta 720
ctccactgtt tagggggtga cttctggaag atagaggcag taactgcagg gagtctgaat 780
gaagaacaaa agaagagaga tgttagagca gttgccagaa aaatttgcct tagagcaagt 840
gtggacttat ttactccagc agagaagata agggactata tatcaagtgt gacaatgaga 900
tttggaacag tagaaagaac gttcgaagac gtaataagaa acagtgatga tatatctgcg 960
gaagtgacct tatgcaaagc ggcacttgga tgcgaattgg gcaaaagcat gagctttggg 1020
aatctaaatc tgaggaaagt cagtggggaa gcagaaacaa tagaaaaaac agtatattgg 1080
ggattaaagc ccataaaata caaatgctgg agaggagagg aaacatttta ttgcgaactg 1140
aggaaagtaa cttgtatgtt tagaaggtct gaaggcctag attgggctaa cattggacct 1200
ggttcacctg aagaaagaag agagctcttg gcaatggtga tgatattctg cagagatggg 1260
agattctttg aatctgcacc agttaatatt gatgaatcat tctttagaac aagactgaat 1320
aaagaaatac cttatcaata tgtgctgcta aaatgggtaa ggcaatcgag agacaacttg 1380
gatgccttgt tgagtacaag aggactgata cctgctcata ttggacaatt cggaaaagga 1440
atgggaatag atggaagtag ctcatcttct atggtttaca agggggtcat gttgtcgaaa 1500
acaccgatag acatagtgga gagcaaagag aagcacaggc tgtttttaaa tgacaatata 1560
gaagcgataa cagagagagg agcaatggtt gcatccataa tggacctatc agaggataat 1620
agagaaacat ttaacgatgt gacttttaac catgtcgact tagctgttct caaagatgaa 1680
aaaactgcaa taataaagat ctatcgatca ctggtggaaa gaataaacac tgatgatgat 1740
ggcctacctg ctttgataat gggtaaaaga tatttagagt tgtatcaatt agatgaagtg 1800
aaagacgcgg tcgggctaat accaaaacgg atgctggggg cgtattccta ccaggcaaga 1860
cagctcatac aatcgcagat caaaaatgac agttatagcc ttcctgaaat aataaaattg 1920
ctgcccttct gttacagccc tccaaagaaa atgttatttg atgggacttt ccatttcaaa 1980
aatcaaatgt atgttaggcc tgggataaac acaaaccttt tcagttttag taagaccgac 2040

-continued

```
aaaagcaaga tatatgtgaa cggaagcgca gtgaaaataa agcttgtgct cggagacgat   2100

gaaatggaca ccagtcttgc ctttgttgaa ggatttcaag tttgtgaata tgatccaaga   2160

gcacctttga taccaagaag agatttgaga ctgattgggt tcggaaagaa agttagagtt   2220

tttgttggtc agggacagga gaaaaccctg gtgaggacga gctccaaaag agccgcctcc   2280

catgatgtaa acaaaaacat tcgtagaatg cgtctggaag tttgaagcac attgaaaaaa   2340

tcctcttgct actgct                                                   2356
```

<210> SEQ ID NO 2
<211> LENGTH: 2261
<212> TYPE: DNA
<213> ORGANISM: Artificial Sequence
<220> FEATURE:
<223> OTHER INFORMATION: cDNA from influenza D virus

<400> SEQUENCE: 2

```
acgtcaatga tatcattgac atacccatac actggggcac ctcctatgtc acatggaaca     60

tcgaccaaat actcaatgga gactgtgtca agaacttact cctacagtag aactaaaaaa    120

gaggtacctt cgggaatatt cccaataaag agaaggaaat tctgtaacac aatagaagac    180

aaagaaaacc tggaaaaacc gaatggaaat gttgatataa atttcatgtt atcgctggca    240

gaaatgctgg aagaaaagat gggaaaaggg ttcttcaaat tctgtgccaa tgaagctgaa    300

gctgaaattt tgaagatgca cttcagcaag ctcactgaag gaaggcaaac ttatgactgg    360

acaagtgaaa gaaatatgcc agcagccacc gctcttcagc taacagtaga cgctatacaa    420

gaaacacagg gaacattcaa aggaactacc atggttgaat attgcaacaa gatattagaa    480

atgatggatt ggccagaagt gaaattcaaa aaggtcagaa tgattgttca gaggcattgg    540

gacccgaaaa ccaaaaaaga aataaaaatg aagtctccaa cattgatgat aacaaagatt    600

ggaagagaag aattcataaa gaggatatgc acgataaaca ccatggccaa agacggagaa    660

agaggaaaat acaaaagaag agctatagcc acccccggga tgggaatcag gccattctca    720

aaaattgtgg aaactttagc acaaaagatt tgtgagagac tagcagagag cggtttgcct    780

gttgggggaa atgagaagaa agccaaacta aaaactacgg tctcttcaac aaactcaaaa    840

ctacaagaag ggcagttcat ggtaaacata acaggggaca acagcaagtg gaatgaatgt    900

cagcaaccag aagcttatct tgcaatgttg gcatacatta ctaaagacag cagcaactta    960

atgaaagatc tctgctcagt agctccaaca ttgttctgca ataagtacgt gaaaatggga   1020

caaggtttcc gagcaaaaaa caaaagaaaa accaaagaaa tagtgatacc cgcaaaaagg   1080

atgaaagaaa ggaaagaatt gatgaacgcg gaatggaggg acctgtttga aacaatagaa   1140

ccttacatgg atggagagtg ctgcttcttg gggggaggaa tgctgatggg aatgtttaac   1200

atgttgtcaa ctgtttttgg agtcatgaca ttaaattaca gggaggaagc attggccaga   1260

aggaactgtt actggactgg gctacaaagt tcagatgatt ttgtgctctt ttgcatctct   1320

aaaacttggc cagagatgga gatgactatt ctaaaattca tcgctgtttg caagttgatg   1380

ggaataaaca tgtctttgga aaaatcctac gggtgcttgc ctgaactttt tgagttcaca   1440

agcatgttct tttccgggga ttttgtctca aacatagcct tggagttacc tgctttcaca   1500

acagctggaa tgaatgaagg aaccgacttc acagctgcga tgtctgtcat aagaacaaac   1560

atgatcaata atggactttc tcctgggact gctttaatgg ccctgcgaat ttgtctgcag   1620

gaatttagag caacatacag agtacaccct tatgactctg gagtgaagaa tcatcgaatg   1680

aaaatcataa ggaaattcat tgaaactatt gaaaacaaag atggattgct gatatcagat   1740
```

-continued

```
ggcgggaaat taatgaacaa tatctcaagt ttgcacatcc ctgaagaaat attgaaagag   1800

gatttgatgg atccctccta caggaacaga gttttcaatc ctaggaaccc ctttacacag   1860

tttgagaaga cagttgacat ctttaaggca agtgggccta taagagtaga ggagaacgaa   1920

gcagttgtat caacgcattc ctttaaaaca aggagcaata ggacattgct aaacacagac   1980

atgagggcaa tggctctcga agagaaaaga taccaagttg tttgcaacat gtaccgatcg   2040

gtcttcgaaa gtgcagacgt taacacccca ataggatcaa tgtcgatggg agaggcaatt   2100

gaagccaaaa tccttgaccg ggccagaacc cagtttgaaa atggaatcat agggggagaa   2160

gaatattctg aaatcaaaag actaatcgag gacgccaagc gtcaacgact gtctgtttaa   2220

gctttgcgtt gtttaataac agaaaaatcc tcttgctact g                       2261
```

```
<210> SEQ ID NO 3
<211> LENGTH: 2194
<212> TYPE: DNA
<213> ORGANISM: Artificial Sequence
<220> FEATURE:
<223> OTHER INFORMATION: cDNA from influenza D virus

<400> SEQUENCE: 3

agcagatatc aggagattta gaaatgtcta gtgtaatcag agaaatcgca aagcgattct     60

tggaacaagc aacgataaac atcgctgaag aagtggtcag agaatatgga gaccatgaaa    120

gaacaatgat atctgttgga gttcatttcc aagcttgctg ccttataagt gatgaatata    180

cccttgagga tgagacaacc ccaagatacg ttcttttgga gggattgaga agacaagagg    240

ctataagcaa gcagaataac atttgctcca ctttgggatt ggaacccttg agaaatctag    300

cagatatttt tgatcgaaaa acaagaagat tccttgaaat aggaattaca aagagagaat    360

ccgatgagta ttaccaggaa aagttcaaca aaataggaaa tgacatggac atacatgttt    420

tcacatatga aggcaaatat ttcagcaaca atcccaatgg gttggaagac atccaaaaga    480

caagaatttt tacattccta tcttttgtgt cagacgaatt gagaaaagag aacatgttca    540

cagaaatgta tgttacagaa gaaggggcac ctgagcttga aatgtacaag tcaaagcttt    600

tcattgcaat gagagacgag agcgtgcctt tgccttacat aaactatgag caccttagga    660

caagatgtga aacattcaaa agaaatcagg ctgaatgcga agcaaaggta gcggatgtgg    720

cttcacggct aaaaatcaaa ctggaacatc tagaagaaaa caaactgcgg ccgctagaga    780

taccgaagga gaaagaggct ccctatacgc acaaatttat gatgaaagat gcttggttct    840

ttgcaaaacc tcatgattcg gagagagcac aaccgcaaca gatattgtat gatttctttg    900

aagcagcaaa catggggttc atgacgacat ccccaaaacc gatattcgga aagcaaggac    960

tgatgtatca ctccctctgg gggcagataa aaagggcaat aaaggacaag agaaatgagt   1020

tggagccttc agaacagagg gacttccttt gtggaattgg aagagcctcc aagaaaatac   1080

aggaggacaa atggcaagaa tccagagagg aagagtttaa acaagaagag actaaagggg   1140

cagctaagag ggggttccca acatggttta atgaagaatg gctttgggca atgagggact   1200

caggggatgg ggacaacaaa ataggggatt ggatacccat ggcagaaatg cctccctgca   1260

agaatgaaat ggaagattat gcaaaaaaga tgtgtgaaga attagaatcc aaaatacagg   1320

gaacaaattg tgctagggaa atgtccaagt tgatacatac aattgggagc ttacatacag   1380

aatgtaggaa ctttcccgga aaggtcaaga tagtgcctat atactgcaga gggacactga   1440

gaggggaatc aactgactgt ttgtttggaa tagcaataaa agggaaatcc catttaaaca   1500

aagatgatgg aatgtatact gttgtaactt ttgagttttc cactgaagaa ccaaatccaa   1560
```

-continued

```
gcaaacatga aaaatatacg gtcttcgaag ctggaacagt gcctgtggaa gccgtggtgt   1620
taactcccaa aagggaaaga gttctcaaag agaagaaatt gtttctttat tgcagaacta   1680
ctggaatgag caagttaaag aacgattggt tttctaaatg caggagatgt cttataccaa   1740
caatggagac tgtagagcag atagtgctga aagaatgcgc tctgaaagaa gaaaacagag   1800
tttcagagat gttggagaat aagagagctt ggattgccca tgagaacgga gagaatctta   1860
caagattggt atcaacaaag ctcaaagact tgtgtagaat gctaattgtg acacaatttt   1920
attactgtat atataacgac aatcagttgg aaggattctg taacgagcaa aagaaattcc   1980
ttatgtttct tcaagcagat aaggactcaa aatctgcatt tacttttaat cagaaagggt   2040
tatatgaaaa aattgaagag tgtattgtca gcaatccatt atgtattttc ctagctgata   2100
ggctgaacaa attatttctt gtagccaagt ccaatggagc taagtacttt gaatgaccaa   2160
aggccttgta atgttaaaaa tctccttgct actg                               2194
```

<210> SEQ ID NO 4
<211> LENGTH: 2049
<212> TYPE: DNA
<213> ORGANISM: Artificial Sequence
<220> FEATURE:
<223> OTHER INFORMATION: cDNA from influenza D virus

<400> SEQUENCE: 4

```
gcagatagca ggagattttc aaagatgttt ttgcttctag caacaattac agcaataact     60
gcttgccaag cagaaagaga actgatatgt atagtgcaaa gagtgaatga aagcttctct    120
cttcactctg gatttggagg aaatgtttac agcatgaaga ctgagccaat gactggattc    180
acaaatgtga ccaaaggtgc tagtgtcatc aaccaaaaag actgggttgg attcggagat    240
tcaaggacag acttgactaa tgctcagttt ccagcgtctt cagatgtccc attggcagtg    300
gcaaagaagt ttaggtcatt gtcaggggct tcgttaatgt tgtcagcttt tggacctcct    360
ggcaaggttg attaccttta tcaaggatgc gggaaagaaa aagtatttta tgaaggggta    420
aactggtccc ctgaggcagg aattgattgc tttgggtcaa actggactca gacaaaaaag    480
gacttctatt cgaggatata tgaagctgct agaggcagca cgtgcatgac ccttgtaaat    540
tctctagaca ccaagatatc atcaaaaaca gccacagctg gaaccacatc ttcttgttct    600
tcaagctgga tgaaaagccc gttgtggtat gcagaatctt ctgttaatcc tggagctaga    660
cctcaagctt gtgggactga gcaatcagca acttttactt tgccgacaag tttcggaatt    720
tacaaatgca acaagcatgt agtgcaactt tgttactttg tgtatgaaaa caaaacagca    780
tttaacactc ttggctgtgg agattattac caaaattact atgacgggaa tggaaacctg    840
gtagggggag tggataacag agtggcagca tacagaggaa tagcaggctc tagagttaaa    900
attgaatgtc cttcaaaaat cttgaaccct gggacttaca gcattagatc aacaccaaaa    960
ttccttctgg taccaaaaag gtcatattgc ttcgacactg atggagggta ccctatacaa   1020
gtggttcaat ctgagtggtc agcttcacga agatcagata atgccactga agaagcatgc   1080
ctacaaacag aaggatgtat tttcatcaaa aagacaaccc cttatgtagg agaagcagat   1140
gacaaccatg gggacattga gatgaggcaa ctcttgagtg ggcttggcaa caacgacaca   1200
gtgtgtgttt cccaaagtgg atacacaaaa ggagagaccc cttttgtaaa ggattatttg   1260
agtcctccca agtatggcag atgtcagttg aaaactgaca gtggaagaat cccaactcta   1320
ccttctgggt tgataatacc gcaagcaggg actgattctt taatgagaac tttgacacca   1380
gcaacaagga tcttcggaat agatgactta gtcttcgggc ttttattcat agggtttgtc   1440
```

-continued gcaggaggag ttgcaggagg ttacttctgg ggaagatcaa gtggaggggg tggtggtgcc 1500
tcggtgagca gtacgcaggc tggatttgac aaaatcggaa aagatataca gcagcttcgg 1560
aatgacacaa atgcagcaat tgaaggcttc aacgggagaa ttgcccatga tgagcaagcc 1620
attaagaatt tggcaaaaga aatcgaagat gcaagggcag aagctttggt aggggaactt 1680
ggtataataa gatccctcat agttgccaac ataagcatga acctaaaaga atctttatat 1740
gaactcgcaa accaaataac aaagagagga ggaggaattg cacaagaagc aggcccaggg 1800
tgttggtatg ttgactccga aaactgtgat gcaagctgca aggagtacat tttcaacttc 1860
aatggcagtg ccactgtccc cacattgagg ccagttgaca ccaatgttgt aataacatcg 1920
gatccttatt acttgggctc gaccatagct ctctgtcttt tgggtctgat ggcgattgct 1980
gcttttgttg gtgtgagttg gatctgttgc aagaaataga atcttagaaa aaatctcctt 2040
gctactgct 2049

<210> SEQ ID NO 5
<211> LENGTH: 1776
<212> TYPE: DNA
<213> ORGANISM: Artificial Sequence
<220> FEATURE:
<223> OTHER INFORMATION: cDNA from influenza D virus

<400> SEQUENCE: 5
agcagatagc aggagattat taagcaatat ggactcaaca aaagcccaaa cgcctgaaga 60
gcaaagagca aagaatgcca aaaccatcct tgagaacata cagatatatg aaaggatgtg 120
tgatctcttt ggggtgtcag aagatgacaa actgataatt gagaacagta tttcaattga 180
gagaatgata agagttgtaa cagataagaa atatcaagac aagaaactaa agaatgctgg 240
aagtgatctt gaaaagattg caaatgcagg gaaagttttc tgccgattgg tggagtcaac 300
agctgggaaa tgtagtgcaa gattgggaat ggcactgaaa cccaacgttg aggcagtcct 360
gaccgatgta ctcgggaatg agctggatag ggctgctgtg cttgggaaaa ggatggggtt 420
tacagcaatg ttcaaatcaa acctggaaga ggttttgtac caaagaggaa agaatcagct 480
taaaaagagg aatgctgcag aaactttcac tctttcacaa ggtgcttcgc tagaggcaag 540
atttaggccc ataatggaaa aacacctagg tgttgggact gttgtggcgt caataaagaa 600
tatcctggca agcaaaaaga acgggaacta caggaacaag atggtgagga aacctggagg 660
aaacagagaa agctggtcac cattggagag agaaatatcc tttctgaaca agaagttgtt 720
tcctggacca atgaggcagc tctgcaagaa attcgaatac ttgaacgacc aagagaagca 780
actggcctta aacctcatgc tggatgcaag tctcatcctg aagccacaag tgactcataa 840
aatgataatg ccttggtcaa tgtggctggc tgtgaagaaa tatgcagaaa tgaacaaggg 900
atcacccagt cttgaagacc tcgcagccta ttctggagta agagccttta tggccttcaa 960
tacagcttgc tacatgagta aattcaccat tgggaaggga attgtgggag atgcagagat 1020
catggaaaat ggaaacgaca agatgcaaac tcttgcaatg gcttgttttg gactggcgta 1080
tgaagacacc gggattgttg cagcaatgat ctcccaaccc atgaagaaaa gatatcagtt 1140
gagggtgggg aacttcaacc ctccagaaga aggaacaata aaaggaacaa gcgccggcta 1200
tttccacaag tgggctgaat ttggaaatag gctgcctttc aacagttttg gaactggtga 1260
atccaaacag ataagcaact caggagtgtt tgcagtgcag aggcccagca ctactaacat 1320
tcaaagactg gcagagctaa tggctaggaa tactggagaa accagcgaca actttactca 1380
gttggttcag aaaataagag aacaagtggg gacctttgct gatcaaaaag caaatcttcg 1440

-continued agagttcacc ggaggatata tttatgatat tactgacgta acgaagagca accccaagat 1500
acctcagttg ggtggggact ctttcttctt tgagttcacc ggaagcgacg ttccaagaac 1560
tggagccaaa agaagagtgg gaggagctga tgatgtgacc cctggaactt cccagcccaa 1620
gaaaagagga aggcaaggtg ccggagcaga atcaagtatg gacattgaaa cagttggtga 1680
agattaactc ttctttggat ggttctgttg cagtccccag tgggtgttaa aggtgttggt 1740
ttgtcttatt taacaaaaaa tctccttgct actgct 1776

<210> SEQ ID NO 6
<211> LENGTH: 1219
<212> TYPE: DNA
<213> ORGANISM: Artificial Sequence
<220> FEATURE:
<223> OTHER INFORMATION: cDNA from influenza D virus

<400> SEQUENCE: 6
agcataagca gaggatattt ttgacgcaat ggcacaagaa caactacttg ctgaacttga 60
gggatacctc agaggaatta acccaatgac caggcaaaca attttgagat ctgcaagagg 120
tggaatggat agcgctaggg atgcagcaag agcagcgaag aagggagaaa tgcaactaac 180
aagtggagag agtatagtgg tgcacatatg cctgagggcc atgtaccctg gaataaagcc 240
atggtcagaa gccaaaaaag atcttgataa agctacagaa ggactgagtg gaaaagacag 300
caaaagcata agaaaggctt tgaggaaggc gggagacctg acagggataa aggagatgat 360
gatgatgtat gaaatgaggg aggacaaaaa agcagaaatg gtggagcaaa tctacgacga 420
tccagaggat tttacagaag atgtaaggct tgggaccgtt gctgcctggc ttcaatgcaa 480
aaacaaaagg agcgagaaat atcatcacaa aatgtcaatg tctggaagca ctgcacttgc 540
cttgggagat gcccaaaaag ctggaatggc catagaaaat atggccagtg ttgtaccaat 600
gaaaaaagag gcccaggcac tgcacaaaga cgcagaagtc ttaattgaac tggcaagaat 660
agcatatggg tcaagagcaa tggaaggaca cctgcaaaat gcaatggacg gaattggaag 720
caaagtcagt ggaatggcta atcttgctct aaaaaggtca gttcttactt tgttaatgtt 780
ggtaatttgt gggatatcca cctgtgtaaa tgctgaaact gtggaagaat tttgtagaaa 840
gaaactaaat cagacggaag aaaaggttta tgtccattgt ttcaatgagg atgatagtcg 900
ggcaatgact ctagctgctt tgatacttgg atgctttagt atgctttaca ttttaataaa 960
ggcaatactg atgcttttgt tgacaatcat aaatggaaga ccaaatggaa gttgggatga 1020
cttgaaacat gttgtaaaat gtttttcaga gactggaagt gagaacttcg ccagggatat 1080
aatggtcctg gagtccaggc gagatgggga ggagacaagc tccctggagg agggactggg 1140
ccctccattg agtggattca atgaaaatgg tgtattcatg gaaacattat aatcgcgaaa 1200
aaatcctctt gctactgct 1219

<210> SEQ ID NO 7
<211> LENGTH: 869
<212> TYPE: DNA
<213> ORGANISM: Artificial Sequence
<220> FEATURE:
<223> OTHER INFORMATION: cDNA from influenza D virus

<400> SEQUENCE: 7
gcagatatca ggggtgtaca atttcaatat gtctgaaaat aagtcagtga acacaacaaa 60
tatcagagca gcaatctccg aattggcatt gggcgcagcc agctggatgg attcctctgg 120
attaatgact ttcgagaaaa tgagaaagtc tgctgagaat tcactgagag tcgaacaggt 180

-continued

```
ttatgaaccg agaacttggg aagatgcagt ggccgaaggt agagaaattc taggattcac    240

tactattgct gccttaagaa aaccagagga gactcatgct gttgaattgg gaaagaacat    300

tatctatccc ttaggaggaa atcctttcta tctgagccca tgtaccattg acactctgta    360

tgagccaaag ctcataagac aaggagaagt cttgggagta aaatatcgga actgcaattg    420

ctttgtaaaa actgctgaac tattagtgac cgacatggga gaaatcattg tgctcttttg    480

cagaaacact gagaaaccag cttactgcct taagaatttc cgtagaggag atgacccaga    540

gaagtcagta cgaaagatac tcagaatttg gagaagtgga cttgttgttg ccgttgatgc    600

ggaatctaga gatgagatca gacgatacaa atctggatgt gaaacagatc ccttctggag    660

aagagaaggc gcaactactg gagaggttca ggagttgctt ggtgtcattg ataaggttga    720

aatccaagct gggagtagcg atggtgaact ctttgactaa ccaggatatg agggccgctt    780

tggatgaaat caagtcagtt tcgagaacaa tttcaatgtt aaaagaatgt attcgttctt    840

tagtatgaaa aaaccccttg ctatctgct                                      869
```

<210> SEQ ID NO 8
<211> LENGTH: 2337
<212> TYPE: DNA
<213> ORGANISM: Artificial Sequence
<220> FEATURE:
<223> OTHER INFORMATION: cDNA from influenza D virus

<400> SEQUENCE: 8

```
tatcgctcgc aaaagagtat gcaaatctca caaaggataa gaaatcatgc aaattgctgt     60

cgcaagggac cgtgtcaagc tacaccactt ttaagaaatg gacaacatcg agaaaagaga    120

aaaacccatc ccttcgaatg agatgggcaa tgggaagcaa gttcccaatc atggcaaaca    180

gagaaatttt ggaagaagct gggataccag aacaatggga agggatagac ctttggtcaa    240

aaaaggatga tgtttcaaag ttggggatgg tgttagcgtc tccagcagcc ataacttact    300

ggaatttttg tggacctgga gtggacaatt cttctgtaat aagggatgtt tacaaagcaa    360

aatttatgaa aaaagagaga tggagagaga ctctgtgggg accaatgaac tttgaactgg    420

tgggtaaaca aagaagaatg gttgaaactc aaccagtgga aataaaacta aaccaaaaag    480

aaataaaaga actgacgatg tgggttcttt ttgaggatga agcaaacctt gcaagtaaat    540

tcatacagga aaatttctca cttgtcctgt cattaagaga actttacaag ggaaaggcag    600

taaataaaga tgttgcagct tttatgattg cacaccaatt ttctcccgag aagaggttct    660

tacccacttt tggccccatt agaccagaaa ggatggagct gctccactgt ttagggggtg    720

acttctggaa gatagaggca gtaactgcag ggagcttgaa tgaagaacaa aagaagagag    780

atgttagagc agttgccaga aaaatttgcc ttagagcaag tgtggactta tttactccag    840

cagagaagat aagggactat atatcaagtg tgacaatgag atttggaaca gtagaaagaa    900

cgttcgaaga cgtaataaga aacagtgatg atatatctgc ggaagtgacc ctatgcaaag    960

cggcacttgg atgcgaattg ggcaaaagca tgagctttgg gaatctaaat ctgaggaaag   1020

tcagtggaga agcagaaaca atagaaaaaa cagtatattg ggattaaag cccataaaat   1080

acaaatgctg gagaggagag gaaacatttt attgcgaact gaggaaagta acttgtatgt   1140

ttagaaggtc tgaaggccta gattgggcta acattggacc tggttcacct gaagaaagaa   1200

gagagctctt ggcaatggtg atgatattct gcagagatgg gagatttttt gaatctgcac   1260

cagttaatat tgatgaatca ttctttagaa caagactgaa taaagaaata ccttatcaat   1320

atgtgctgct aaaatgggta aggcaatcga gagacaactt ggatgccttg ttgagtacaa   1380
```

-continued

```
gaggactgat acctgctcat attggacaat ttggaaaagg aatgggaata gatggaagta   1440

gctcatcttc tatggtttac aagggagtca tgttgtcgaa gacaccgata gacatagtgg   1500

agagcaaaga gaagcacagg ttgtttttaa atgacaatat agaagcgata acagagagag   1560

gagcaatggt tgcatccata atggacctat cagaggataa tagagaaaca tttaacgatg   1620

tgacttttaa ccatgtcgac ctagctgttc tcaaagatga aaaaactgca ataataaaga   1680

tctatcgatc actggtggaa agaataaaca ctgatgatga tggcctacct gctttgataa   1740

tgggtaaaag atatttagag ttgtatcaat tagatgaagt gagagacgcg gtcgggctaa   1800

taccaaaacg gatgctgggg gcgtattcct accaggcaag acagctcata caatcgcaga   1860

tcaaaaatga cagttatagc cttcctgaaa taataaagtt gctgcccttc tgttacagcc   1920

ctccaaagaa aatgttattt gatgggactt tccatttcaa aaatcaaatg tatgttaggc   1980

ctgggataaa cacaaacctt ttcagtttta gtaagaccga caaaagcaag atatatgtga   2040

acggaagcgc agtgaaaata aagcttgtgc tcggagacga tgaaatggac accagtcttg   2100

cctttgttga aggatttcaa gtttgtgaat atgatccaag agcacctttg ataccaagaa   2160

gagatttgag actgattggg ttcggaaaga aagttagagt tttgttggt cagggacagg   2220

agaaaaccct ggtgaggacg agctccaaaa gagccgcctc ccatgatgta agcaaaaaca   2280

ttcgtagaat gcgtctggaa gtttgaagca cattgaaaaa atcctcttgc tactgct      2337
```

<210> SEQ ID NO 9
<211> LENGTH: 2307
<212> TYPE: DNA
<213> ORGANISM: Artificial Sequence
<220> FEATURE:
<223> OTHER INFORMATION: cDNA from influenza D virus

<400> SEQUENCE: 9

```
caatggaaat aaacccatat ctactcatgc taaacaatga tataacgtca atgatatcat     60

tgacataccc atatactggg gcacctccta tgtcacatgg aacatcgacc aaatactcaa    120

tggagactgt gtcaagaact tactcctaca gtagaactaa aaaagaggta ccttcgggaa    180

tattcccaat agagagaagg aaattctgta acacaataga agacaaagaa aacctggaaa    240

aaccgaatgg aaatgttgat ataaatttca tgttatcgct ggcagaaatg ctggaagaaa    300

agatggggaa agggtttttc aaattctgtg ccaatgaagc tgaagctgaa attttgaaga    360

tgcacttcag caagctcact gaaggaaggc aaacttatga ctggacaagt gaaagaaata    420

tgccagcagc caccgctctt cagctaacag tagacgctat acaagaaaca cagggaacat    480

tcaaaggaac taccatggtt gaatattgca acaagatatt agaaatgatg gattggccgg    540

aagtgaaatt caaaaaggtc agaatgattg ttcagaggca ttgggacccg aaaaccaaaa    600

aagaaataaa aatgaagtct ccaacattga tgataacaaa gattggaaga gaagaattca    660

taaagagaat atgcacgata aataccatgg ccaaagacgg agaaagagga aaatacaaaa    720

gaagagctat agccaccccc gggatgggaa tcaggccatt ctcaaaaatt gtggaaactt    780

tagcacaaaa gatttgtgag agactagcag agagcggttt gcctgttggg ggaaatgaga    840

agaaagccaa actaaaaact acggtctctt caacaaactc aaaactacaa gaagggcagt    900

tcatggtaaa cataacaggg gacaacagca agtggaatga atgtcagcaa ccagaagctt    960

atcttgcaat gttggcatac attactaaag acagcagcaa cttaatgaaa gatctctgct   1020

cagtagcacc aacattgttc tgcaataagt atgtaaaaat gggacaaggt ttccgagcaa   1080

aaaacaaaag aaaaaccaaa gaaatagtga tacccgcaaa aaagatgaaa gaaaggaaag   1140
```

-continued

```
aattgatgaa cgcggaatgg agggacctat ttgaaacaat agaaccttac atggatggag   1200
agtgctgctt cttgggggga ggaatgctga tgggaatgtt taacatgttg tcaactgttt   1260
ttggagtcat gacattaaat tacagggagg aagcattggc caaaaggaac tgttactgga   1320
ctgggctaca aagttcagat gattttgtgc tcttttgcat ctctaggact tggccagaga   1380
tggagatgac tattctaaaa ttcatcgctg tttgcaagtt gatgggaata aacatgtctt   1440
tggaaaaatc ctacgggtgc ttgcctgaac tttttgagtt cacaagcatg ttcttttccg   1500
gggattttgt ctcaaacata gcattggagt tacctgcttt cacaacagct ggaatgaatg   1560
aaggaaccga cttcacagct gcgatgtctg tcataagaac aaacatgatt aataatggac   1620
tttctcctgg gactgcttta atggccctgc gaatttgtct gcaggaattt agagcaacat   1680
acagagtaca cccttatgat tctggagtga agaatcatcg aatgaaaatc ataaggaaat   1740
tcattgaaac tattgaaaac aaagatggat tgctgatatc agatggcggg aaattaatga   1800
acaatatctc aagtttgcac atccctgaag aaatattgaa agaggatttg atggatccct   1860
cctacaggaa cagagttttc aatcctagga accccttttac acagtttgag aagacagttg   1920
acatctttaa ggcaagtgga cctataaggg tagaggagaa cgaggcagtt gtatcaacgc   1980
attcctttag aacaaggagc aataggacat tgctaaatac agacatgagg gcaatggctc   2040
tcgaagagaa aagataccaa gttgtttgca acatgtaccg atcggtcttc gaaagtgcag   2100
acgttaacac cccaatagga tcaatgtcga tgggagaggc aattgaagcc aaaatccttg   2160
accgggccag aacccagttt gaaaatggaa tcataggggg agaagaatat tctgaaatca   2220
aaagactaat cgaggacgcc aagcgtcaac gactgtctgt ttaagctttg cgttgtttaa   2280
taacagaaaa atcctcttgc tactgct                                       2307
```

```
<210> SEQ ID NO 10
<211> LENGTH: 2196
<212> TYPE: DNA
<213> ORGANISM: Artificial Sequence
<220> FEATURE:
<223> OTHER INFORMATION: cDNA from influenza D virus

<400> SEQUENCE: 10
```

```
agcagatagc aggagattta gaaatgtcta gtgtaatcag agaaatcgca aagcgattct     60
tggaacaagc aacgataaac atcgctgaag aagtggtcag agaatatgga gaccatgaaa    120
gaacaatgat atctgttgga gttcatttcc aagcttgctg ccttataagt gatgaatata    180
cccttgagga tgagacaacc ccaagatacg ttcttttgga gggattgaaa agacaagagg    240
ctataagcaa gcagaataac atttgctcca ctttgggatt ggagcccttg agaaatctag    300
cagatatttt tgatcgaaaa acaaaaagat tccttgaggt aggaattaca aggagagaat    360
ccgatgagta ttaccaggaa aagttcaaca aaataggaaa tgacatggac atacatgttt    420
tcacatatga aggcaaatac ttcagcaaca atcccaatgg gttggaagac atccaaaaga    480
caagaatttt tacattccta tcttttgtgt cagacgaatt gagaaaagag aacatgttca    540
cagaaatgta tgttacagaa gaaggggcac ctgagcttga aatgtacaag tcaaagcttt    600
tcattgcgat gagagacgag agcgtgcctt tgccttacat aaactatgag caccttagaa    660
caagatgtga aacattcaaa agaaatcagg ctgaatgcga agcaaaggta gcggatgtgg    720
cttcacggct aaaaatcaaa ctggaacatc tagaagaaaa taaactgcgg ccgctagaga    780
taccgaagga gaaagaggct ccctatacac acaaattttt gatgaaagat gcttggttct    840
ttgcaaaacc tcatgattcg gagagagcac aaccgcaaca gatattgtat gatttctttg    900
```

aagcagcaaa catggggttc atgacgacat ccccaaaacc gatattcgga aagcaaggac 960
tgatgtatca ctccctctgg gggcagacaa aaagagcaat aaaggacaag agaaatgagt 1020
tggagccttc agaacagaga gacttccttt gtggaattgg aagagcctcc aagaaaatac 1080
aggaggacaa atggcaagaa tccagagagg aagagtttaa acaagaagag actaaagggg 1140
cagctaagag ggggttccca acatggttta atgaagaatg gctttgggca atgagggatt 1200
caggggatgg ggacaataaa ataggggatt ggatacccat ggcagaaatg cctccttgca 1260
agaatgagat ggaagattat gcaaaaaaga tgtgtgaaga attagaatcc aaaatacagg 1320
gaacaaattg tgctagggaa atgtccaagt tgatacatac aattgggagc ttacatacag 1380
aatgtaggaa ctttcccgga aaggtcaaga tagtgcctat atactgcaga gggacactga 1440
gaggggaatc aactgactgt ttgtttggaa tagcaataaa agggaaatcc catttaaaca 1500
aagatgatgg aatgtatact gttgtaactt ttgagttttc cactgaagaa ccaaatccaa 1560
gcaaacatga aaaatatacg gtcttcgaag ctggaacagt gcctgtggaa gccgtggtgt 1620
taactcccaa aagggaaaga gttctcaaag agaagaaatt gttcctttat tgcagaacta 1680
ctggaatgag caagttaaag aacgattggt tttctaaatg caggagatgt cttataccaa 1740
caatggagac tgtagagcag atagtgctga aagaatgcgc tctgaaagaa gaaaacagag 1800
tttcagagat gttggagaat aagagagctt ggattgccca tgagaacgga gagaatctta 1860
caagattggt atcaacaaag ctcaaagact tgtgtagaat gctaattgtg acacaatttt 1920
attactgtat atataatgac aatcaattgg aaggattctg taacgagcaa aagaaattcc 1980
ttatgtttct tcaagcagat aaggactcaa aatctgcatt tacttttaat cagaaagggt 2040
tatatgaaaa aattgaagag tgtattgtca gcaatccatt atgtattttc ctagctgata 2100
ggctaaacaa attatttctt gtagccaagt ccaatggagc taagtacttt gaatgaccaa 2160
aggccttgta atgttaaaaa tctccttgct actgct 2196

<210> SEQ ID NO 11
<211> LENGTH: 2045
<212> TYPE: DNA
<213> ORGANISM: Artificial Sequence
<220> FEATURE:
<223> OTHER INFORMATION: cDNA from influenza D virus

<400> SEQUENCE: 11
gcagatagca ggagattttc aaagatgttt ttgcttctag caacaattac agcaataact 60
gcttgccaag cagaaagaga actgatatgc atagtgcaaa gagtgaatga aagcttctct 120
cttcactctg gatttggagg aaatgtttac agcatgaaga ctgagccaat gactggattc 180
acaaacgtga ccaaaggtgc tagtgtcatc aaccaaaaag actggattgg attcggagat 240
tcaagaacag acttgaataa tgatcagttt ccagcgtctt cagatgttcc attggcagtg 300
gcgaagaagt ttcggtcatt gtcaggggct tcgctgatgt tgtcagcttt tgggcctcct 360
ggcaaggttg actacctcta tcaaggatgt gggaaagaga aagtatttta tgaaggggta 420
aactggtccc ctgaggcagg aattgattgc tttggatcaa actggactca gacaaagaag 480
gacttctatt cgaagatata tgaagctgct agaagcagca catgcatgac tcttgtaaat 540
tctcttgaca ccaagatatc atcaacaaca gctacggctg gaaccgcatc ttcttgttct 600
tcaagttgga tgaaaagccc gttgtggtat gcagaatctt ctgttaatcc tggagctaaa 660
cctcaagttt gtgggactga gcaatcggca acttttactt tgccgacaag cttcggaatt 720
tacaaatgca acaagcatgt agtgcagctt tgttactttg tatacgaaaa caaaacaaca 780

-continued

```
tttaacactt ttggctgtgg agattattac caaaattact atgatgggaa tggaaacctg    840

atagggggaa tggataacag agtggcagca tacagaggaa tagcaaacgc tggagttaaa    900

attgaatgtc cttccaaaat cttgaaccct gggacttaca gcattagatc aacaccaaga    960

ttcctcctag taccaaaaag gtcatactgc ttcgacactg atggagggta ccctatacaa   1020

gtagttcaat ctgagtggtc agcttcacga agatcagata atgccacaga agaagcatgc   1080

ctacaaacag aaggatgtat tttcatcaaa aagacaaccc cttatgtagg agaagcagat   1140

gacaaccatg gagacattga gatgaggcaa ctcttgagtg ggcttggcaa caatgacaca   1200

gtgtgcgttt cccaaagtgg atacacaaaa ggagagaccc cttttgtaaa ggattatttg   1260

agtcctccca agtatggcag atgtcagttg aaaactgaca gtggaagaat cccaactcta   1320

ccttctgggt tgataatacc gcaagcaggg actgactctt taatgacaac tttgacgcca   1380

gcaacaagga tcttcggaat agatgactta atcttcgggc ttttattcgt ggggtttgtc   1440

gcaggagggg tcgcaggagg ttacttctgg ggaagatcaa atggaagggg tggtggtgcc   1500

tcggtgagca gtacgcaggc tggatttgac aaaatcggaa aagatataca gcagcttcgg   1560

aatgacacaa atgcagcaat tgaaggcttc aacgggagaa ttgcccatga tgagcaagcc   1620

attaagaatt tggcaaaaga aatcgaagat gcaagggcag aggctttggt aggggaactt   1680

ggtataataa gatccctcat agttgccaac ataagcatga atctaaaaga atctttatat   1740

gaactagcaa accaaataac aaaaagagga ggaggaattg cacaagaagc aggcccaggg   1800

tgttggtatg ttgactccga aaactgtgat gcaagctgca aagagtacat tttcaacttc   1860

aatggaagtg ccactgtccc cacattgagg ccagttgaca ccaaggttgt aataacatcg   1920

gatccttatt acttgggttc gaccatagct ctctgtcttt tggggctggt ggcgattgct   1980

gcttctgttg gtgtgatttg gatctgttgc aagaaataga atcttagaaa aaatctcctt   2040

gctac                                                               2045
```

```
<210> SEQ ID NO 12
<211> LENGTH: 1774
<212> TYPE: DNA
<213> ORGANISM: Artificial Sequence
<220> FEATURE:
<223> OTHER INFORMATION: cDNA from influenza D virus

<400> SEQUENCE: 12

agcagatagc aggagattat taagcaatat ggactcaaca aaagcccaaa cgcctgaaga     60

gcagagagca aagaatgcca aaaccatcct tgagaacata cagatatatg aaaggatgtg    120

tgatctcttt ggggtgtcag aagatgacaa actgataatt gagaacagta tttcaattga    180

gagaatgata agagttgtaa cagataagaa ataccaagac aaaaaactaa agaatgccgg    240

aagtgatcct gaaaagattg caaatgcagg gaaagttttc tgtcgattgg tggagtcaac    300

agctgggaaa tgtagtgcaa gattgggaat ggcactgaaa cccaacgttg aggcagtcct    360

gaccgatgta ctcgggaatg aactggatag ggctgctgtg cttgggaaaa gaatggggtt    420

ttcagcaatg ttcaaatcaa acctggaaga ggttttgtac caaagaggaa agaatcagct    480

taaaaagagg aatgctgcag aaactttcac tctttcacaa ggtgcttcgc tagaggcaag    540

atttaggccc ataatggaaa aacacctagg tgttgggact gttgtggcgt caataaagaa    600

tatcctggca agcaaaaaga acgggaacta caggaacaag atggtgagga aacctggagg    660

aaacagagag agctggtcac cattggagag agagatatcc tttctgaaca agaagctgtt    720

tcctggacca atgaggcagc tctgcaagaa attcgaatac ttgaacgacc aagagaagca    780
```

-continued

```
actggcctta aaccttatgc tggatgcaag tctcatccta aaaccgcaag tgactcacaa    840
aatgataatg ccttggtcaa tgtggctggc tgtgaagaag tatgcagaaa tgaacaaggg    900
atcacccagt cttgaagacc tcgcagccta ttctggagta agagccttta tggccttcaa    960
tacagcttgc tacatgagta aattcaccat tgggaaggga attgtgggag atgcagagat   1020
catggaaaat ggaaacgaca agatgcaaac tcttgcaatg gcttgttttg gactggcgta   1080
tgaagacacc gggattgttg ctgcaatgat ctcccaaccc atgaagaaaa gatatcagtt   1140
gagagtgggg aacttcaatc ctccagaaga aggaacaata aaaggaacaa gcgccggcta   1200
tttccacaag tgggctgaat ttggaaatag gctgcctttc aacagttttg gaactggtga   1260
atccaaacag ataagcaact caggagtgtt tgcagtgcag aggcccagca ctactaacat   1320
tcaaagactg gcagagctaa tggctaggaa taccggagaa accagcgaca actttactca   1380
gttggttcag aaaataagag aacaagtggg ggcctttgct gatcaaaaag caaatcttcg   1440
agagttcacc ggaggatata tttatgacat tactgacgta acgaagagca accccaagat   1500
acctcagttg ggtggggact ctttcttctt tgaattcacc ggaagcgacg ttccaagaac   1560
tggagccaaa agaagagtgg gaggagctga tgatgtgacc cctggaactt cccagcccaa   1620
gaaaagagga aggcaaggtg ccggagcaga atcaagtatg gacattgaaa cagttggtga   1680
agattaactc atctttggat ggttctgttg cagtccccag tgggtgttaa aggtgttggt   1740
ttgtcttatt taacaaaaaa tctccttgct actg                               1774
```

<210> SEQ ID NO 13
<211> LENGTH: 1218
<212> TYPE: DNA
<213> ORGANISM: Artificial Sequence
<220> FEATURE:
<223> OTHER INFORMATION: cDNA from influenza D virus

<400> SEQUENCE: 13

```
gcagaagcag aggatatttt tgacgcaatg gcacaagaac aactacttgc tgaacttgag     60
ggatacctca gaggagttaa cccaatgacc aggcaaacga ttatgaagtc tgcaagaggt    120
gggatggata gtgctaagga ggcagcaaaa gcagcgaaga agggagaaat gcaactaaca    180
agtggagaga gcatagtggt gcacatatgc ctgagagcca tgtaccctgg aataaagcca    240
tggtcagaag ccaaaaaaga tcttgataaa gctacagaag gactgagtgg aaaagacagc    300
aaaaatataa gaaaagctct gaggaaggca ggagacctga cagggataaa ggagatgatg    360
atgatgtatg aaatgaggga ggacaaaaaa gcagaaatgg tagagcaaat ctacgatgac    420
ccagaggatt ttacagaaga tgtaaggctt gggaccgttg ctgcctggct tcaatgcaaa    480
aacaaaagga gcgagaaata tcatcacaag atgtcaatgt ctggaagcac tgcacttgcc    540
ttgggagatg cccaaaaggc cggaatggcc atagaaaata tggctagtgt tgtgccaatg    600
aaaaaagagg cccaggcact gcacaaagac gcagaagttt tgattgaact ggcaagaata    660
gcatatgggt caagagcaat ggaagggcac ctgcaaaatg caatggacgg aattggaagc    720
aaagtcagtg gaatggctaa tcttgcccta aaaaggtcag ttcttacttt gttaatgttg    780
gtaatttgtg ggatccccac ttgtgtaaat gctgaaactg tggaagaatt ttgtagaaag    840
aaactaaatc agacggaaga aaaggtttat gtccattgtt tcaatgagga tgatggtcgg    900
gcaatgactt tagctgcttt gatacttgga tgctttagta tgctttacat tttaataaag    960
gcaatactga tgcttttgtt gacaatcata aatggaagac caaatggaaa ttgggatgac   1020
ttgaaacatg ttgtaaaatg tttttcagag actggaagtg agaacttcgc cagggatata   1080
```

-continued atggtcctgg aatccaggcg agatggggag gagacaagct ccccagagga gggactaggc 1140
cctccattga gtggattcaa tgaaaatggt gtattcatgg aaacattata atcgcgaaaa 1200
aatcctcttg ctactgct 1218

<210> SEQ ID NO 14
<211> LENGTH: 869
<212> TYPE: DNA
<213> ORGANISM: Artificial Sequence
<220> FEATURE:
<223> OTHER INFORMATION: cDNA from influenza D virus

<400> SEQUENCE: 14
gcagatagca ggggtgtaca atttcaatat gtctgaaaat aagtcagtga acacaacaaa 60
tatcagagca gcaatctccg aattggcatt gggcgcagcc agctggatgg attcctctgg 120
gttaatgact ttcgagaaaa tgagaaagtc tgctgagaat tcactgagag tcgaacaggt 180
ttatgaaccg agaacttggg aagatgcagt ggctgaaggt agagaaattc taggattcac 240
tactattgct gccttaagaa aaccagagga gactcatgct gttgaattgg ggaagaacat 300
tatctatccc ttaggaggaa accctttcta tctaagccca tgtaccattg acactctgta 360
tgagccaaag ctcataagac aaggagaagt ctttggagta aaatatcgga actgcaattg 420
ctttgtaaaa actgctgaac tattagtgac cgacatggga gaaatcattg tgctcttttg 480
cagaaacact gagaaaccag cttactgcct taagaatttc cgtagaggag atgacccaga 540
gaagtcagta cgaaagatac tcagaatttg gagaagtgga cttgttgttg ccgttgatgc 600
ggaatctaga gatgaaatca gacgatacaa atctggatgt gaaacagatc ccttctggag 660
aagagaaggc gcaactactg gagaggttca ggagttgctt ggtgtcatta ataaggttga 720
aatccaagct gggagtagcg atggtgaact ctttgactaa ccaggatatg agggccgctt 780
tggatgaaat caagtcagtt tcgagaacaa tttcaatgtt aaaagaatgt attcgttctt 840
tagtatgaaa aaaccccttg atatctgct 869

<210> SEQ ID NO 15
<211> LENGTH: 2364
<212> TYPE: DNA
<213> ORGANISM: Artificial Sequence
<220> FEATURE:
<223> OTHER INFORMATION: cDNA from influenza D virus

<400> SEQUENCE: 15
agcagaagca gaggatgtca ctactattaa cgctcgcaaa agagtatgca aatctcacaa 60
aggataagaa atcatgcaaa ttgctgtcgc aagggaccgt gtcaagctac accactttta 120
agaaatggac aacatcgaga aaagagaaaa acccatccct tcgaatgaga tgggcaatgg 180
gatctaagtt tccgataatg gctaatagag aaatactcga agaggcaggg atacccgaac 240
aatgggaagg tatagatcta tggagtaaaa aagacgatgt gtctaagtta gggatggtgt 300
tagcgtcacc tgcagcaata acgtattgga atttttgtgg tccaggagtg gataactcta 360
gcgtaattag ggatgtgtat aaagcgaaat ttatgaaaaa agagagatgg agagagacac 420
tatggggtcc tatgaatttc gaactcgtag ggaaacaacg gagagtagta gaaacgcaac 480
ccgttgagat aaaactgaat caaaaagaga taaaggaatt gactatgtgg gtgctattcg 540
aagacgaagc gaatctggct agtaaattta tacaggaaaa ctttagctta gtgttgtcac 600
ttagggaatt gtataagggg aaggcagtga ataaagacgt agcagcattt atgatagcac 660
accaatttag tcccgaaaaa agattcttac ctacattcgg acctattaga cccgaaagaa 720

-continued tggaattgtt gcattgctta gggggggatt tttggaaaat cgaagcggtt accgcaggat 780
cacttaacga ggagcagaaa aaaagagacg ttagggcagt cgctagaaag atatgcctta 840
gagctagcgt tgatctgttt acacctgccg aaaaaattag ggattacata tctagcgtta 900
ctatgagatt cggaacagtc gaaagaacat tcgaagacgt aattaggaat agcgatgata 960
taagcgcaga agtgacacta tgtaaagcag cattaggttg cgaattgggg aagtctatgt 1020
cattcggaaa tcttaacctt agaaaggtta gcggagaagc cgaaactatc gaaaaaacag 1080
tgtattgggg acttaagcct ataaaatata aatgttggag aggcgaagag acattctatt 1140
gcgaacttag aaaagtgaca tgcatgttta gacgatccga agggttagat tgggctaaca 1200
tagggccagg atcacccgaa gagagaaggg aattgctcgc aatggttatg atattttgta 1260
gagacggaag atttttcgaa agcgcaccag tgaatataga cgaatcattt tttagaacta 1320
gacttaacaa agagatacca taccaatacg tactgcttaa atgggttagg caatctaggg 1380
ataacttaga cgcactattg tcaactaggg gactgatacc cgcacatata gggcaattcg 1440
gaaagggaat ggggatagac ggatctagta gtagttctat ggtgtataag ggagtgatgc 1500
tatctaagac acctatcgat atagtcgaat cgaaagagaa acatagattg ttccttaacg 1560
ataacataga ggcaataacc gaaagaggcg caatggttgc gtcaattatg gatcttagcg 1620
aagataatag ggaaactttt aacgatgtga cattcaatca cgttgatcta gccgtactga 1680
aagacgaaaa aactgcgata attaagatat atagatcact agtcgaaaga ataaatactg 1740
acgatgacgg actgccagca ctgataatgg gaaagagata tctcgaattg tatcaattgg 1800
acgaagtgaa agacgccgtg ggactgatac ctaaaagaat gttaggcgca tactcatatc 1860
aggctagaca attgatacaa tcgcaaatta aaaacgatag ttatagtctg ccagagataa 1920
taaaactgtt accattttgt tatagtccac ctaaaaaaat gctattcgac ggaacttttc 1980
actttaaaaa ccaaatgtac gttagaccag ggataaatac taatctgttt agcttttcga 2040
aaaccgataa gtctaagata tacgttaacg gatccgcagt taagataaag ttagtgttag 2100
gcgatgacga aatggatact agtctcgcat tcgttgaggg atttcaggtc tgcgaatacg 2160
atcctagagc accactgata ccaagaagag atttgagact gattgggttc ggaaagaaag 2220
ttagagtttt tgttggtcag ggacaggaga aaaccctggt gaggacgagc tccaaaagag 2280
ccgcctccca tgatgtaagc aaaaacattc gtagaatgcg tctggaagtt tgaagcacat 2340
tgaaaaaatc ctcttgctac tgct 2364

<210> SEQ ID NO 16
<211> LENGTH: 2330
<212> TYPE: DNA
<213> ORGANISM: Artificial Sequence
<220> FEATURE:
<223> OTHER INFORMATION: cDNA from influenza D virus

<400> SEQUENCE: 16
agcagaagca gaggatttta taacaatgga aataaaccca tatctactca tgttaaacaa 60
tgatataacg tcaatgatat cattgacata cccatacact ggggcacctc ctatgtcaca 120
tggaacatcg accaaatact caatggagac tgtgtcaaga acttactcct acagtagaac 180
taaaaaagag gtaccttcgg gaatattccc aataaagaga aggaaattct gtaacacaat 240
agaagacaaa gaaaacctgg aaaaaccgaa tggaaatgtt gatataaatt tcatgttatc 300
gttagccgaa atgttagagg aaaaaatggg aaagggtttc tttaaatttt gcgctaacga 360
agccgaagcc gaaatactga aatgcactt tagcaagttg accgaaggta gacagacata 420

-continued

```
cgattggact agtgaacgaa atatgccagc cgcaaccgca ttgcaattga cagtcgacgc    480
tatacaggaa acacagggga cattcaaagg gactactatg gtcgaatact gtaataagat    540
actcgaaatg atggattggc ctgaagtgaa attcaaaaaa gttagaatga tagtgcaacg    600
acattgggat cctaagacta aaaaagagat taaaatgaaa agtcctacat tgatgattac    660
gaaaatcgga agagaggaat tcataaaaag gatatgcaca atcaatacta tggctaaaga    720
cggagagaga gggaagtaca aaagaagggc aatcgctaca cctggaatgg ggattaggcc    780
attctctaag atagtcgaaa cattagcgca aaagatatgc gaaaggttag ccgaatccgg    840
attgcccgta gggggaaacg aaaaaaaggc taagcttaag actaccgtta gtagtactaa    900
ctctaagttg caggaagggc aatttatggt taacataaca ggcgataact caaaatggaa    960
cgaatgccag caaccggaag catacttagc tatgttggca tacataacga aagactcatc   1020
taaccttatg aaagacctat gtagcgttgc gccaacattg ttttgcaata aatacgttaa   1080
gatgggacag ggggtttaggg ctaaaaacaa acgaaaaact aaagagatag tgatacccgc   1140
taagagaatg aaagagagaa aagagttgat gaacgctgaa tggagagacc tattcgaaac   1200
aatcgaacca tacatggacg gagagtgttg tttcttagga ggggggatgt tgatgggaat   1260
gttcaatatg ctatcaaccg tattcggagt tatgacactt aactataggg aagaggcact   1320
agctagacga aattgttatt ggacagggtt gcaatctagc gacgatttcg tactgttttg   1380
catatctaag acatggcctg aaatggaaat gacaatactg aaattcatag ccgtatgcaa   1440
attgatgggg attaacatgt cactcgaaaa atcatacgga tgcttacccg aattgttcga   1500
attcacttca atgtttttta gcggagattt cgtttcgaat atcgcactcg aattgcctgc   1560
attcactacc gcaggaatga acgagggaac cgatttcaca gccgcaatgt ccgttattag   1620
gactaacatg attaataacg gactgtcacc aggaaccgca ttgatggcac ttaggatatg   1680
cttgcaggaa tttagggcta catacagagt gcatccatac gatagcggag tgaaaaacca   1740
tagaatgaaa attattagga aatttatcga aacaatcgaa aacaaagacg gactattgat   1800
tagcgacgga gggaaattga tgaataacat atctagtcta cacatacccg aagagatact   1860
gaaagaggat ctgatggacc catcatatag gaatagggtt tttaacccta gaaacccatt   1920
tacgcaattc gaaaagacag tcgacatatt caaagctagc ggacctatta gggtcgaaga   1980
gaacgaagcc gttgtgtcaa cacactcatt caaaactagg tctaatagga cactactgaa   2040
taccgatatg agagctatgg cactcgaaga gaaaagatac caagtcgtat gcaatatgta   2100
tagatccgta ttcgaatccg cagacgttaa cacacctatc ggatcaatgt cgatgggaga   2160
ggcaattgaa gccaaaatcc ttgaccgggc cagaacccag tttgaaaatg gaatcatagg   2220
gggagaagaa tattctgaaa tcaaaagact aatcgaggac gccaagcgtc aacgactgtc   2280
tgtttaagct ttgcgttgtt taataacaga aaaatcctct tgctactgct               2330
```

<210> SEQ ID NO 17
<211> LENGTH: 2195
<212> TYPE: DNA
<213> ORGANISM: Artificial Sequence
<220> FEATURE:
<223> OTHER INFORMATION: cDNA from influenza D virus

<400> SEQUENCE: 17

```
agcagaagca ggagatttag aaatgtctag tgtaatcaga gaaatcgcaa agcgattctt     60
ggaacaagca acgataaaca tcgctgaaga agtggtcaga gaatatggag accatgaaag    120
aacaatgata tctgttggag ttcatttcca agcttgctgc cttataagtg atgaatatac    180
```

-continued

```
cttggaggac gaaactacac ctagatacgt actgttggag ggattgagac ggcaagaggc    240
aatatccaaa cagaataaca tttgttcaac attggggttg gaacccctta gaaacctagc    300
cgatatattc gatagaaaga ctaggagatt cttagagata gggattacga aaagggaatc    360
cgacgaatat tatcaagaga aattcaataa gatagggaac gatatggaca tacatgtgtt    420
tacatacgaa gggaaatatt tttccaataa ccctaacgga ttggaagaca tacaaaaaac    480
taggattttt acattcctat cattcgtttc cgacgaattg agaaaagaga atatgtttac    540
ggaaatgtac gttaccgaag agggagcacc cgaactcgaa atgtataagt ctaagttgtt    600
catagctatg agagacgaat ccgttccctt accctatatt aattacgaac atcttagaac    660
tagatgcgaa acattcaaac ggaatcaggc agaatgcgaa gctaaagtgg cagacgtagc    720
tagcagactg aaaattaagc ttgagcatct cgaagagaat aagcttagac ccttagagat    780
accgaaagag aaagaggcac catatacaca taagtttatg atgaaagacg catggttttt    840
cgctaaacca cacgattccg aaagagcgca accgcaacag atactatacg atttttttcga    900
agcagctaat atggggttta tgacaacatc ccctaagcct atattcggaa aacagggatt    960
gatgtatcat agcctatggg ggcaaattaa gagagcaatt aaggataaga gaaacgaact   1020
cgaacctagc gaacagagag actttctttg cggaataggg agagctagca aaaagataca   1080
agaggataaa tggcaagagt ctagggaaga ggaattcaaa caggaagaga ctaagggagc   1140
agctaaaagg gggtttccga catggtttaa cgaagaatgg ttatgggcta tgagggatag   1200
cggagacgga gacaataaga taggcgattg gatacctatg gccgaaatgc caccatgtaa   1260
aaacgaaatg gaggattacg ctaaaaaaat gtgcgaagag ttagagtcta agatacaggg   1320
aactaattgc gctagggaaa tgtcaaaact gatacataca atagggtcat tgcatacaga   1380
gtgtagaaac tttcccggaa aggttaagat agtgccaatt tattgtagag ggacacttag   1440
gggggaatca actgattgcc tattcggaat cgcaattaag ggaaaatccc atcttaacaa   1500
agacgacgga atgtatacag ttgtgacatt cgaattctca actgaggaac ctaatccctc   1560
aaaacacgaa aagtatacgg tattcgaagc aggaacagtg ccagtcgaag ccgtagtgtt   1620
gacacctaag agagagagag tgcttaaaga gaaaaaattg tttttgtatt gtagaacaac   1680
agggatgtca aaactgaaaa acgattggtt ttcgaaatgt agacgatgtc tgataccgac   1740
aatggagaca gtcgaacaga tagtgcttaa ggaatgcgca cttaaggaag agaatagggt   1800
tagcgaaatg cttgagaata agagagcatg gatcgcacac gaaaacggag agaatctgac   1860
tagattggtg tcaactaagc ttaaagacct atgtagaatg ttgatagtga cacaattcta   1920
ttattgtata tataacgata accaattgga ggggttttgt aacgaacaga aaaaattcct   1980
tatgtttttg caggcagata aggattccaa atccgcattt acttttaatc agaaagggtt   2040
atatgaaaaa attgaagagt gtattgtcag caatccatta tgtattttcc tagctgatag   2100
gctgaacaaa ttatttcttg tagccaagtc caatggagct aagtactttg aatgaccaaa   2160
ggccttgtaa tgttaaaaat ctccttgcta ctgct                              2195
```

<210> SEQ ID NO 18
<211> LENGTH: 2049
<212> TYPE: DNA
<213> ORGANISM: Artificial Sequence
<220> FEATURE:
<223> OTHER INFORMATION: cDNA from influenza D virus

<400> SEQUENCE: 18
agcagaagca ggagattttc aaagatgttt ttgcttctag caacaattac agcaataact 60
gcttgccaag cagaaagaga actgatatgt atagtgcaaa gagtgaatga aagcttctct 120
cttcactctg ggttcggtgg taacgtatac tctatgaaaa ccgaacctat gacagggttt 180
actaacgtta ctaagggggc tagtgtaatt aaccaaaagg attgggtcgg gttcggagac 240
tctaggaccg atcttactaa cgcacaattt cccgcatcat ctgacgtacc attagcagtc 300
gcaaaaaaat ttagatcgct atctggagca tcacttatgc ttagcgcatt cggcccacca 360
ggaaaggttg actatttgta tcagggatgt ggaaaggaaa aagtgtttta cgaaggagtt 420
aattggtcac ctgaagccgg catcgattgt ttcggatcta attggacaca aactaaaaaa 480
gacttttact ctagaatata cgaagccgct aggggatcga catgcatgac attggttaac 540
tcacttgaca ctaagattag ttcgaaaacc gctacagccg gaactactag ttcatgttca 600
tctagttgga tgaaatcacc attgtggtat gctgaatcta gcgttaaccc aggagctagg 660
ccgcaagcat gcggcactga gcaatccgct acatttacat tgcctacatc attcggaata 720
tataagtgta ataagcatgt agtgcaattg tgttatttcg tatacgaaaa caaaaccgca 780
ttcaatacgt taggttgcgg agactattat cagaattatt acgacggaaa cggaaacctc 840
gtgggggGaa tggacaatag agtcgcagca tatagggGga tagccggatc aggagttaaa 900
atcgaatgcc ctagcaagat acttaatccc ggcacatact caattaggtc tacacctaaa 960
tttctgttag tgcctaagag gtcatattgt ttcgatacag acggagggta tccgatacag 1020
gtagtgcaat ccgaatggtc agctagtaga agatccgata acgcaaccga agaggcatgc 1080
ttgcagactg agggatgtat ttttattaaa aaaactacac catacgtagg agaagcagac 1140
gataatcatg gcgatatcga aatgagacaa ttgttgtcag ggttagggaa taacgatacc 1200
gtatgcgttt cgcaatctgg gtatactaaa ggcgaaacac cattcgttaa ggattatctg 1260
tcaccaccta aatacggtag atgtcaattg aaaaccgata gcggcagaat acctacattg 1320
cctagcggat tgattatacc gcaagccgga actgactcac ttatgcggac attgacacct 1380
gcaactcgaa tattcggaat agacgattta gtgttcggac tattgttcat agggttcgtt 1440
gcaggaggcg tcgcaggggg gtatttttgg ggtagatcta gcggaggggg agggggagct 1500
agcgttagta gtacacaagc cggattcgat aagataggga aggatataca gcaacttagg 1560
aacgatacta acgcagcaat cgaagggttt aacggtagaa tcgcacatga cgaacaggca 1620
attaagaatc tcgctaaaga gatagaggac gctagagccg aagcactcgt aggcgaattg 1680
gggataatta gatcattgat cgttgcgaat atatctatga atcttaaaga gtcactatac 1740
gaactagcta accaaattac gaaaagagga gggggaatcg cacaagaggc aggacctgga 1800
tgttggtatg ttgatagcga aaattgcgac gctagttgta aagagtatat ttttaacttt 1860
aacggatccg caacagtgcc tacacttagg ccagtcgata ctaacgtagt gattactagt 1920
gatccttatt acttgggctc gaccatagct ctctgtcttt tgggtctgat ggcgattgct 1980
gcttttgttg gtgtgagttg gatctgttgc aagaaataga atcttagaaa aaatctcctt 2040
gctactgct 2049

<210> SEQ ID NO 19
<211> LENGTH: 1775
<212> TYPE: DNA
<213> ORGANISM: Artificial Sequence
<220> FEATURE:
<223> OTHER INFORMATION: cDNA from influenza D virus -continued

<400> SEQUENCE: 19

```
agcagaagca ggagattatt aagcaatatg gactcaacaa aagcccaaac gcctgaagaa     60
caaagagcaa agaatgccaa aaccatcctt gagaacatac agatatatga aaggatgtgt    120
gatctctttg gagttagtga agacgataaa ttgataatag aaaactcaat tagtatcgaa    180
agaatgatta gggtggtgac cgataaaaag tatcaggata agaaactgaa aaacgcaggt    240
tccgatctgg aaaaaatcgc taacgcaggg aaggtgtttt gtagactggt ggagtcaact    300
gccggaaagt gtagcgctag actgggaatg gcacttaagc ctaacgttga ggcagtgttg    360
actgacgtac tgggtaacga actcgatagg gccgcagtgt tgggaaagag aatgggtttt    420
accgctatgt tcaaatctaa tctcgaagag gttctgtatc agagagggaa gaaccaactg    480
aaaaagagaa acgctgcaga gacattcaca ctgtcacagg gtgctagtct tgaggctagg    540
tttagaccaa ttatggagaa acacctaggg gttggaaccg tagtcgctag tattaagaat    600
atactcgcta gcaagaaaaa cggtaactat aggaataaga tggttaggaa acccggaggg    660
aatagggagt catggtcacc ccttgagaga gagattagct ttctgaataa aaaactgttt    720
cccggaccta tgcgacaatt gtgcaaaaaa ttcgaatacc ttaacgatca ggaaaagcaa    780
ttggcattga accttatgct tgacgctagt ctgatactga aaccacaagt gacacataag    840
atgattatgc catggtcaat gtggttagcc gttaagaaat acgctgagat gaataaggga    900
tcaccctcac tcgaagacct agccgcatat tccggcgtga gagcgtttat ggcattcaat    960
accgcatgct atatgtcaaa gtttactatc ggaaagggga tcgtgggaga cgcagagatt   1020
atggaaaacg gaaacgataa gatgcagaca ctagctatgg catgcttcgg actggcatac   1080
gaagataccg gaatagtggc agcaatgata tcccaaccta tgaaaaaacg ttatcaattg   1140
agagttggaa actttaaccc acccgaagag ggaactatta agggaactag cgcagggtat   1200
tttcacaaat gggccgaatt cggaaataga ctgccattca atagtttcgg aactggagaa   1260
tcgaaacaga ttagcaatag cggagtgttc gcagtgcaac gacctagtac tactaacata   1320
cagagactag ccgaattgat ggctaggaat accggagaga ctagcgataa ctttacgcaa   1380
ttggtgcaaa agattaggga acaggttgga acattcgcag accaaaaggc taaccttagg   1440
gaattcacag gggggtatat atacgatata actgacgtta ctaagtctaa ccctaagata   1500
ccccaactcg ggggggattc attctttttc gaatttaccg gatccgacgt acctagaacc   1560
ggagcgaaaa gaagggttgg gggggcagac gacgttactc ccggaactag ccaacctaaa   1620
aaaaggggga gacagggagc cggagcagaa tcaagtatgg acattgaaac agttggtgaa   1680
gattaactct tctttggatg gttctgttgc agtccccagt gggtgttaaa ggtgttggtt   1740
tgtcttattt aacaaaaaat ctccttgcta ctgct                              1775
```